US007060435B1

(12) United States Patent
Paulussen et al.

(10) Patent No.: US 7,060,435 B1
(45) Date of Patent: Jun. 13, 2006

(54) GENOTYPING CYTOCHROME EXPRESSION

(75) Inventors: Aimée Dymphne Catherine Paulussen, Tilburg (NL); Martin Armstrong, Wickambreaux (GB)

(73) Assignee: Janssen Pharmaceutica, Beerse (BE)

( * ) Notice: Subject to any disclaimer, the term of this patent is extended or adjusted under 35 U.S.C. 154(b) by 0 days.

(21) Appl. No.: 09/869,169

(22) PCT Filed: Dec. 22, 1999

(86) PCT No.: PCT/GB99/04380

§ 371 (c)(1),
(2), (4) Date: Jun. 22, 2001

(87) PCT Pub. No.: WO00/39332

PCT Pub. Date: Jul. 6, 2000

(30) Foreign Application Priority Data

Dec. 23, 1998 (GB) ................................ 9828619.8

(51) Int. Cl.
*C12Q 1/68* (2006.01)
*C12P 19/34* (2006.01)
*C07H 21/04* (2006.01)
*C12N 9/02* (2006.01)

(52) U.S. Cl. ......................... 435/6; 435/91.2; 435/189; 536/23.2; 536/23.5; 536/24.31; 536/24.33

(58) Field of Classification Search .................... 435/6, 435/19, 91.2; 536/23.2, 23.5, 24.31, 24.33
See application file for complete search history.

(56) References Cited

FOREIGN PATENT DOCUMENTS

| | | | |
|---|---|---|---|
| EP | 0463395 A1 | 1/1992 | |
| EP | 0759476 A1 | 2/1997 | |
| WO | WO 00/39332 A1 | 7/2000 | |

OTHER PUBLICATIONS

Jounaidi, Y et al. Sequence of the 5'-flanking region of cyp3a5: comparative anaylsis with cyp3a4 and cyp3a7. Biochem. Biophys. Res. Comm. 205(3):1741-1747 (Dec. 1994).*

Aoyama, T., et al., "Cytochrome P450 hPCN3 a novel cytochrome P450IIIA gene product that is differentially expressed in adult human liver", J.Biol. Chem. 1989 264:10388-10395.

Barwick JL., et al., "Trans-species gene transfer for analysis of glucocorticoid-inducible transcriptional activation of transiently expressed human CYP3A4 and rabbit CYP3A6 in primary cultures of adult rat and rabbit hepatocytes" Molecular Pharmacology, 1996 50:10-16.

Boobis A.R., et al., "Dissecting the function of cytochrome P450" Br. J. Clin. Pharmacol. 1996 42:81-89.

(Continued)

*Primary Examiner*—Diana B. Johannsen

(57) ABSTRACT

There is disclosed a method of identifying subjects having a high or low drug metabolising phenotype associated with cytochrome CYP3A5 expression, which method comprises screening genomic DNA from said subject for the presence or absence of one or more polymorphic variants in a transcription regulatory region of the sequence encoding CYP3A5. Oligonucleotide molecules for carrying out the screening are also provided.

2 Claims, 15 Drawing Sheets

OTHER PUBLICATIONS

Cholerton, S., et al., "The role of individual human cytochrome P450 in drug metabolism and clinical response" Trend Pharmac. Sci. 1992 13:434-439.
Fujii-Kuriyama, et al., "Regulation of CYP1A1 expression" FASEB J. 1002 6:706-710.
Gorski, J.C., et. al., "Regioselective biotransformation of midazolam by members of the human cytochrome P450 (CYP3A) subfamily", Biochem. Pharmacol. 1994 9:1643-1653.
Guengerich, F.P. "Characterisation of human cytochrome P450 enzymes", FASEB 1992 6:745-748.
Hashimoto, H., et al. "Gene structure of CYP3A4, an adult specific form of cytochrome P450 in human livers and its transcriptional control", Eur. J. Biochem. 1993 218:585-595.
Haehner, B.D. et al. "Bimodal distribution of renal cytochrome P450 3A activity in humans", Mol. Pharmacol., 1996 50:52-59.
Hoffman, E.C., et al. "Cloning of a factor required for activity of the Ah (dioxin) receptor", Science, 1991 252:954-958.
Hoyo-Vadillo, C. et al. "Pharmacokinetics of nifedipine slow release tablets in Mexican subjects: further evidence for an oxidative polymorphism", J. Clin. Pharmac. 1989 29:816-820.
Imataka, H., et al., "Cell specific translational control of transcription factor BTEB expression. The role of an upstream AUG in the 5' untranslated region", J. Biol. Chem. 1994 269:20668-73.
Itoh, S., et al. "Genomic organization of human fetal specific P-450IIIA7 (cytochrome P-450HFLa)- related gene (s) and interaction of transcriptional regulatory factor with its DNA element in the 5' flanking region", Biochimica et Biophysia Acta. 1992 1130:133-138.
Jounaidi, Y., et al., "Sequence of the 5'-flanking region of CYP3A5 comparative analysis with CYP3A4 and CYP3A7", Biochem. Biophys. Res. Commun. 1994 205:1741-1747.
Kormori M. et al. "Fetus specific expression of a form of cytochrome P-450 in human livers", Biochemistry 1990 29:4430-4433.
Lavrijsen K., et al. "Induction potential of antifungals containing an imidazole or triazole moiety. Miconazole and ketoconazole, but not itraconazole are able to induce hepatic drug metabolising enzymes of male rats at high doses", Biochem. Pharmacol. 1986 35:1867-78.
Miller, G.L. "Protein determination for large numbers of samples", Anal. Chem. 1959 31:964.
Nebert, D.W. The Ah locus: genetic differences in toxicity, Cancer, mutation and birth defects. Critical Reviews in Toxicology, 20, 153-174 (1989).
Renwick, A.G., et al., "The pharmacokinetics of oral nifedipine—a population study", Br. J. Clin. Pharmcol. 1988 25:701-708.
Schellens, J.H.M., et al., "Lack of bimodality nifedipine plasma kinetics in a large population of healthy subjects", Biochem. Pharmacol. 1988 37:2507-2510.
Schuetz, J., et al, "Selective expression of cytochrome P450 CYP3A mRNAs in embryonic and adult human liver", Pharmacogenetics, 1994 4:11-20.
Shimada, T., et al, "Evidence for cytochrome P-450NF, the nifedipine oxidase, being the principal enzyme involved in the bioactivation of aflatoxins in human liver", Proc. Natl. Acad. Sci. USA 1989 86:462-465.
Sogawa, K., et al, "Comparison of DNA-binding properties between BTEB and Sp1 (1)". J. Biochem, 1993 114:605-9.
Watkins, P.B. "Drug metabolism by cytochromes P450 in the liver and small bowel", Gastroenterology Clinics of North America, 1992 21:511-526.
Wrighton, S.A. et al. "Studies in the expression and metabolic capabilities of human liver cytochrome P450IIIA5 (HLp3)". Mol. Pharmacol. 1990 38:207-213.
Rannug, A., et. al. "Genetic Polymorphism of Cytochromes P450 1A1, 2D6 and 2E1: Regulation and Toxicological Significance", JOEM 37(1) 1995 pp. 25-36.
Jounaidi, Y., et. al. "Detection of a CYP3A5 Allelic Variant: A Candidate for the Polymorphic Expression of the Protein?" Biochemical and Biophysical Research Communication 1996 221:466-470.
Meyer, Urs., et al. "Molecular Mechanisms of Genetic Polymorphisms of drug metabolism", Annual Rev. Pharmacol. Toxicol, 1997, 37:269-96.
Paulussen, Aimee, et al. "Two linked mutations in transcriptional regulatory elements of the CYP3A5 gene constitute the major genetic determinant of ploymorphic activity in humans", Pharmacogenetics, 2000 10:415-425.
Chou, Fang-Chun, et. al. "Genetic polymorphism of cytochrome P450 3A5 in Chinese", DMD 2001 29:1205-1209.
Kuehl, P., et al. "Sequence diversity in CYP3A promoters and characterization of the genetic basis of polymorphic CYP3A5 expression", Nature Genetics 2001 27:383-391.
Schuetz, E. G. et al., "Modulators and Substrates of P-glycoprotein and Cytochrome P4503A Coordinately Upregulate these Proteins in Human Colon Carcinoma Cells", Molecular Pharmacology 1996 49:311-318.
Yokoi, T., "Genetic Polymorphism of Drug Metabolizing Enzymes: New Mutations in CYP2D6 and CYP2A6 Genes in Japanese", Pharmaceutical Research 1998 vol. 15 No. 4 517-524.
Gilles, P.N., et al "Single nucleotide polymorphic discrimination by an electronic dot blot assay on semiconductor microchips", Nat. Biotech, 1999 17:365-370.
Patinen, T., et al. "Minisequencing: A Specific Tool for DNA Analysis and Diagnostics on Oligonucleotide Arrays" Genome Res. 1997 7:606-614.
Underhill, P.A., et al. "A pre-Columbian Y chromosome-specific transition and its implications for human evolutionary history" PNAS USA 1996, 93:196-200.
Medline: Accession No. 1998428039, Abstract of Nippon Yakurigaku Zasshi. Folia Pharmacologica Japonica, 112 (1) 5-14. 1998 Ref:45 Journal code: F2X. ISSN: 0015-5691.
Roskey, M. T., et al., "DNA sequencing by delayed extraction-matrix-assisted laser desorption/ionization time of flight mass spectrometry", Proc. Natl. Acad. Sci. USA, 1996 vol. 93:4724-4729.
Shumaker, J.M. et al., "Mutation Detection by Solid Phase Primer Extension", Human Mutation 1996 7:346-354.
Bunce, M., et al, "Comprehensive, serologically equivalent DNA typing for HLA-B by PCR using sequence-specific primers (PCR-SSP)", Tissue Antigens 1995 45:81-90.
Bunce, M., et al. "Phototyping: comprehensive DNA typing for HLA-A, B, C, DRB1, DRB3, DRB4, DRB5 & DQB1 by PCR with 144 primers mixes utilizing sequence-specific primers (PCR-SSP)", Tissue Antigens 1995 46:355-367.

* cited by examiner

CYP3A5 Genotype/Phenotype Relationship

CYP3A5 mRNA Expression Related to Genotype

FIG. 2.
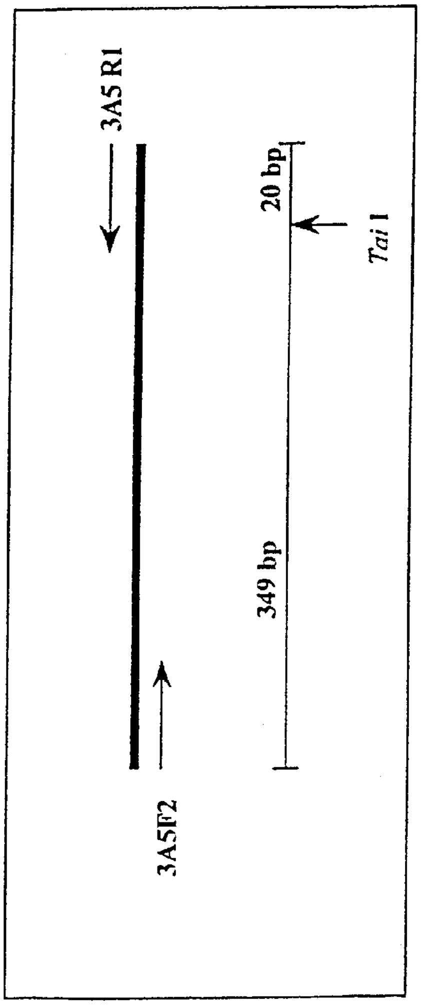
2a.
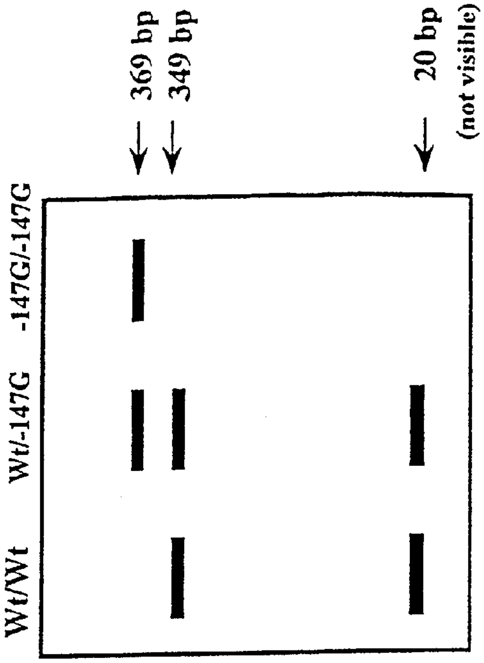
2b.
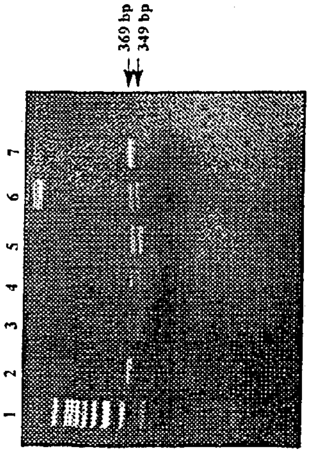
2c.

3a.
3a.
3A5F2
3A5 R1
18 bp
318 bp
33 bp
Alu I
Alu I
3b.
Wt/Wt
Wt/-475G
-475G/-475G
336 bp
318 bp
33 bp
3c.
1 2 3 4 5 6 7 8 9
336 bp
318 bp
X
33 bp
500 bp
300 bp
100 bp

FIG. 6.

3A5F1 5’-GGGTCTGTCTGGCTGCGC-3’

3A5F2 5’-GGGGTCTGTCTGGCTGAGC-3’

3A5R1 5’TTTATGTGCTGGAGAAGGACG-3’

FIG. 7

```
-1343 GGAAGCAACC TACATGTCCA TCAACAGATG AATGGGTAAA GAGAGTACTT CACTTATGCA CAATGGAGTA
-1273 CAATTCAGCC ATGAAAAAAG CATGAGATCC TGTCCTTTAT AATAACGTGG CTGGAACTGC AGGTCATTAT
-1203 GTTAGGTAAA ATAAGCCAGG CACACAAAGA CAGACATTGC ATGTTCTCAC TTATTTGTGG GATCTACAAA
-1133 TCAAAACAAT TGAGCTAATG TCTGGGTCTT AGTCAATTTT GTACCCTAAG TACAGGGAGC ACAGCCATTA
-1063 GAATACATGA TGAATGCTTT AATACAGGAA TGAATAGGTG AGAGGCACAG GGTGGTTGGG TGTTCTTCTG
-993  ATACATAGTA TCTTCCTTGA CACATTCAGT ACAACTCTCA ACAGGTAAGT CTCTTCATGT ATGTTACCTT
-923  CTGAGGAATT AAGTGGCAGA ACATGCCTTC TATTATTTTC CTTTGCAGAA CAAGACCAAT TGCATTAGTT
-853  GGGAAACAGT GCTGGCTGCA TCTGAGCCCC AAGCAACCAT TAGTCTATTG CTATCACCAC AGACTCAGAG
-783  GGGATGACAC ACAGGGGCCC AGCAATCTCA CCCAAGTCAA CTCCACCAAC ATTTCTGGTC ACCCACCATG
-713  TGTACAGTAC CCTGCTAGGG TCCAGGGTCA TGAAAGTAAA TAATACCAGA CTGTGCCCTT GAGGAACTCA
-643  CCTCTGCTAA GGGAAACAGG CACAGAAACC CACAAGGGTG GTAGAGAGGA AATAGGACAA TAGGACTGTG
-573  TGAGGGGGAT AGGAGGCACC CAGAGGAGGA AATGGTTACA TCTGTGTGAG GAGGTTGGTA AGGAAAGACT
-503  TTAATAGAAG GGGTCTGTCT GGCTGGGCTT GCAAGGATGT GTAGGAGTCA TCTAGGGGGC ACAAGTACAC
-433  TCCAGGCAGA GGGAATTGCA TGGGTAAAGA TCTGCAGTTG TGGCTTGTGG GGATGGATTT CAAGTATTCT
-363  GGAATGAAGA CAGCCATGGA AACAAGGGCA GGTGAGAGGA TATTTAAGAG GCTTCATGCC AATGGCTCCA
-293  CTTCAGTTTC TGATAAGAAC TCAGGTTCCG TGGACTCCCT GATAAAACTG ATTAAGTTGT TTATGATTCC
-223  CCATAGAATA TGAACTCAAA GGAGGTAAGC AAAGGGGTGT GTGCGATTCT TTGCTACTGG CTGCAGCTGC
```

FIG. 7(CONTINUED)

```
-153  AGCCCCACCT CCTTCTCCAG CACATAAACA TTTCAGCAGC TTGACCTAAG ACTGCTGTGC AGGGCAGGGA
-83   TGCTCCAGGC AGACAGCCCA GCAAACAACA GCACACAGCT GAAAGTAAGA CTCAGAGGAG ACAGTTGAAG
-13   AAGGCAAGTG GCGATG
```

Variant Sequences in the 5' flanking region of CYP3A5

| Position | Variant sequence | Percentage |
|---|---|---|
| -1317 | G-K (T or G) heterozygote | 2.8% (1/36) |
| -988 | T-Y (C or T) heterozygote | 8.3% (3/36) |
| -657 | C-Y (C or T) heterozygote | 8.3% (3/36) |
| -475 | T-K (T or G) heterozygote | 30.6% (11/36) |
| -264 | G-R (G or A) heterozygote | 2.8% (1/36) |
| -147 | A-R (A or G) heterozygote | 30.6% (11/36) |

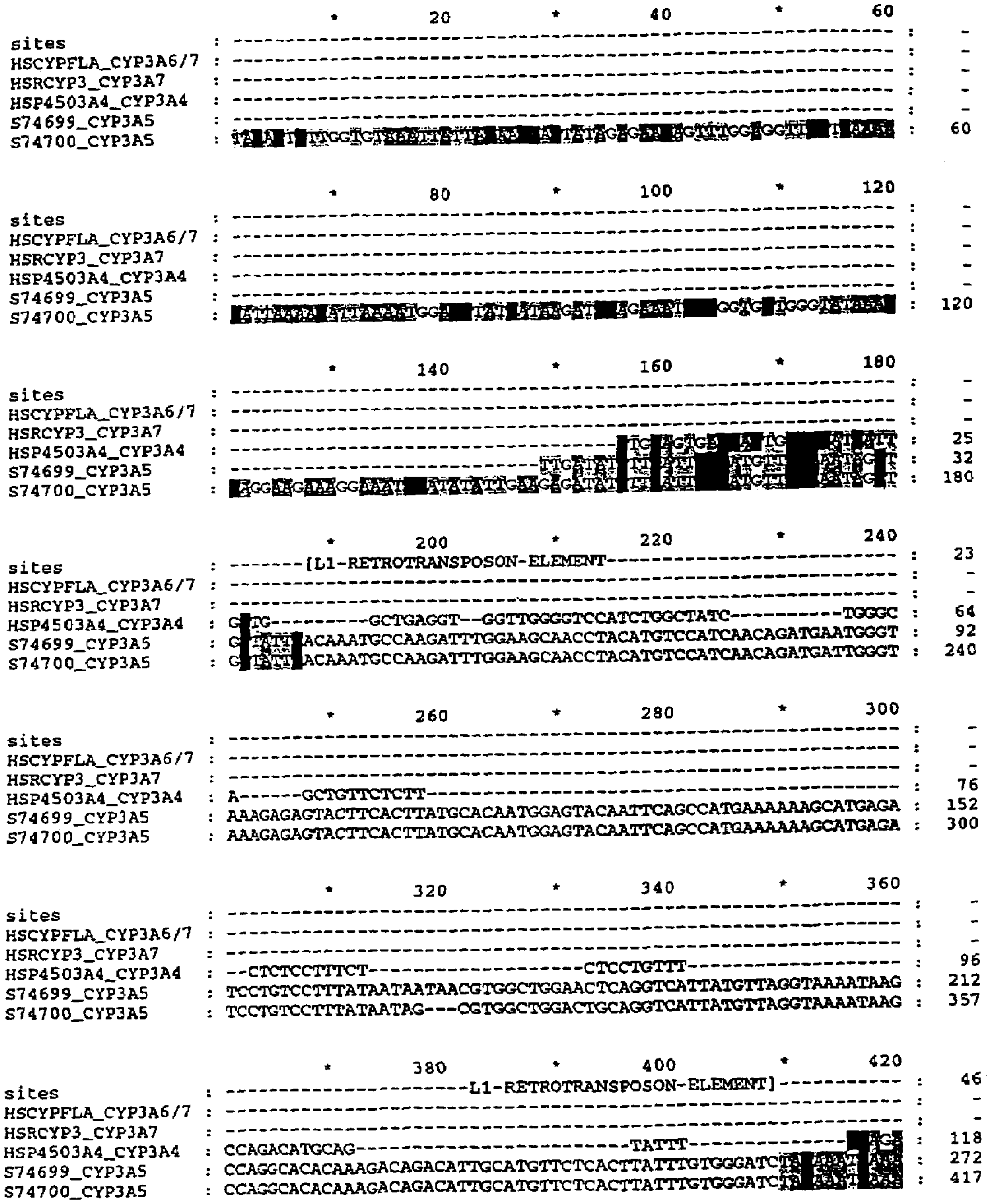

FIG. 9a

CYP3A4, CYP3A5, CYP3A6/7

```
                              *        20         *        40         *        60
sites            : ------------------------------------------------------------ :   -
HSCYPFLA_CYP3A6/7: ------------------------------------------------------------ :   -
HSRCYP3_CYP3A7   : ------------------------------------------------------------ :   -
HSP4503A4_CYP3A4 : ------------------------------------------------------------ :   -
S74699_CYP3A5    : ------------------------------------------------------------ :   -
S74700_CYP3A5    : [████████████████████████████████████████████████████████████]:  60

                              *        80         *       100         *       120
sites            : ------------------------------------------------------------ :   -
HSCYPFLA_CYP3A6/7: ------------------------------------------------------------ :   -
HSRCYP3_CYP3A7   : ------------------------------------------------------------ :   -
HSP4503A4_CYP3A4 : ------------------------------------------------------------ :   -
S74699_CYP3A5    : ------------------------------------------------------------ :   -
S74700_CYP3A5    : [████████████████████████████████████████████████████████████]: 120

                              *       140         *       160         *       180
sites            : ------------------------------------------------------------ :   -
HSCYPFLA_CYP3A6/7: ------------------------------------------------------------ :   -
HSRCYP3_CYP3A7   : ------------------------------------------------------------ :   -
HSP4503A4_CYP3A4 : -------------------------------------TC▓▓G▓▓▓A▓▓G▓▓▓▓▓▓▓▓▓TT :  25
S74699_CYP3A5    : ----------------------------------------------▓▓▓▓▓▓▓▓▓▓▓▓▓▓T :  32
S74700_CYP3A5    : [▓▓G▓▓G▓▓▓GG▓▓▓▓ ▓▓▓▓▓▓▓▓▓G▓G▓▓▓▓▓▓▓▓ ▓ ▓▓▓▓▓▓▓▓▓▓▓▓▓▓▓▓▓▓▓T]: 180

                              *       200         *       220         *       240
sites            : -------[L1-RETROTRANSPOSON-ELEMENT--------------------------- :  23
HSCYPFLA_CYP3A6/7: ------------------------------------------------------------ :   -
HSRCYP3_CYP3A7   : ------------------------------------------------------------ :   -
HSP4503A4_CYP3A4 : G▓▓G----------GCTGAGGT--GGTTGGGGTCCATCTGGCTATC---------TGGGC :  64
S74699_CYP3A5    : G▓▓▓▓ACAAATGCCAAGATTTGGAAGCAACCTACATGTCCATCAACAGATGAATGGGT :  92
S74700_CYP3A5    : G▓▓▓▓ACAAATGCCAAGATTTGGAAGCAACCTACATGTCCATCAACAGATGATTGGGT : 240

                              *       260         *       280         *       300
sites            : ------------------------------------------------------------ :   -
HSCYPFLA_CYP3A6/7: ------------------------------------------------------------ :   -
HSRCYP3_CYP3A7   : ------------------------------------------------------------ :   -
HSP4503A4_CYP3A4 : A------GCTGTTCTCTT----------------------------------------- :  76
S74699_CYP3A5    : AAAGAGAGTACTTCACTTATGCACAATGGAGTACAATTCAGCCATGAAAAAAGCATGAGA : 152
S74700_CYP3A5    : AAAGAGAGTACTTCACTTATGCACAATGGAGTACAATTCAGCCATGAAAAAAGCATGAGA : 300

                              *       320         *       340         *       360
sites            : ------------------------------------------------------------ :   -
HSCYPFLA_CYP3A6/7: ------------------------------------------------------------ :   -
HSRCYP3_CYP3A7   : ------------------------------------------------------------ :   -
HSP4503A4_CYP3A4 : --CTCTCCTTTCT-------------------CTCCTGTTT------------------ :  96
S74699_CYP3A5    : TCCTGTCCTTTATAATAATAACGTGGCTGGAACTCAGGTCATTATGTTAGGTAAAATAAG : 212
S74700_CYP3A5    : TCCTGTCCTTTATAATAG---CGTGGCTGGACTGCAGGTCATTATGTTAGGTAAAATAAG : 357

                              *       380         *       400         *       420
sites            : --------------------L1-RETROTRANSPOSON-ELEMENT]------------- :  46
HSCYPFLA_CYP3A6/7: ------------------------------------------------------------ :   -
HSRCYP3_CYP3A7   : ------------------------------------------------------------ :   -
HSP4503A4_CYP3A4 : CCAGACATGCAG-----------------------TATTT-------------▓▓ : 118
S74699_CYP3A5    : CCAGGCACACAAAGACAGACATTGCATGTTCTCACTTATTTGTGGGATC▓▓▓▓ : 272
S74700_CYP3A5    : CCAGGCACACAAAGACAGACATTGCATGTTCTCACTTATTTGTGGGATC▓▓▓▓ : 417
```

FIG. 9a (CONTINUED 1).
CYP3A4, CYP3A5, CYP3A6/7
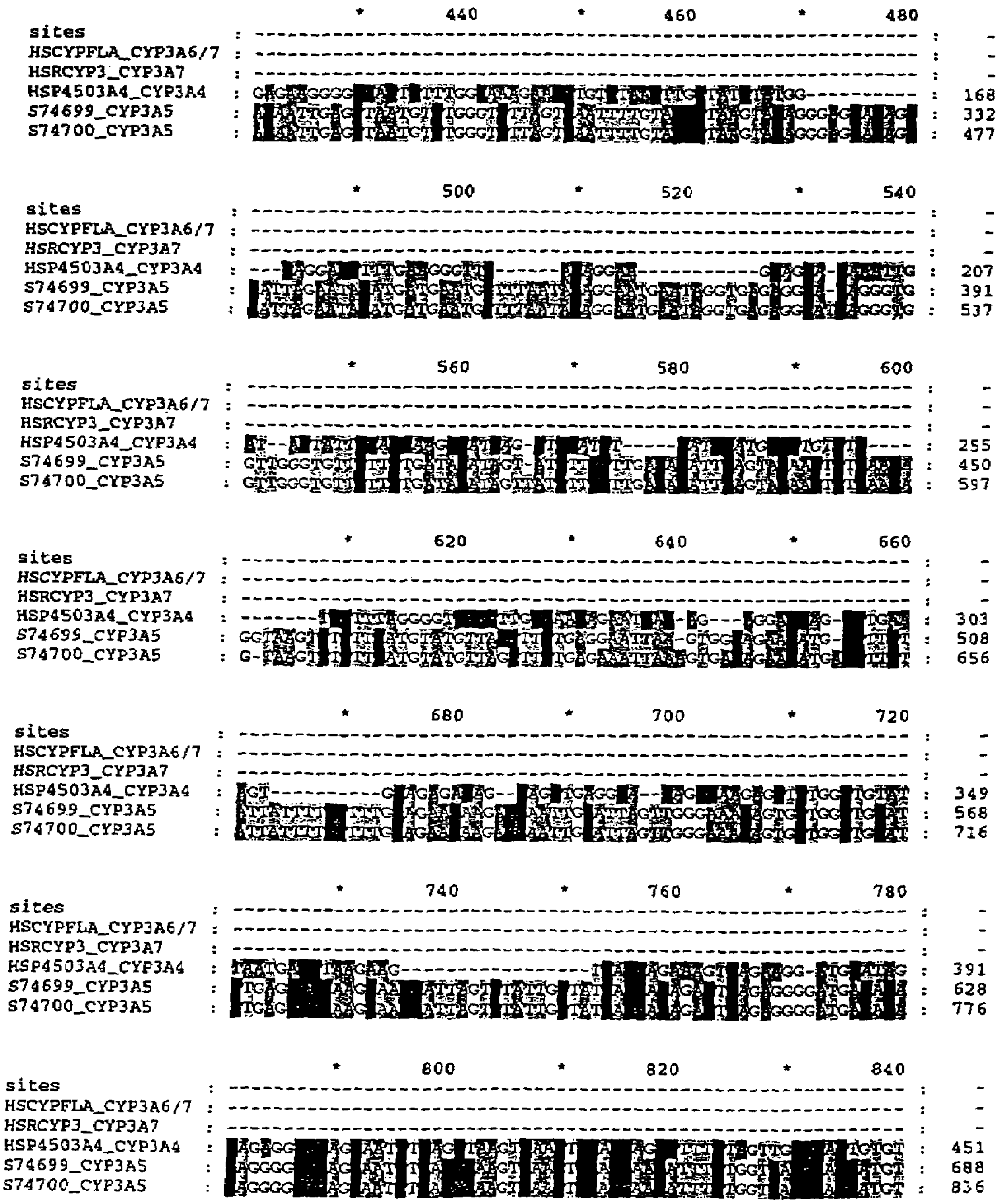

FIG. 9a (CONTINUED 2)

CYP3A4, CYP3A5, CYP3A6/7

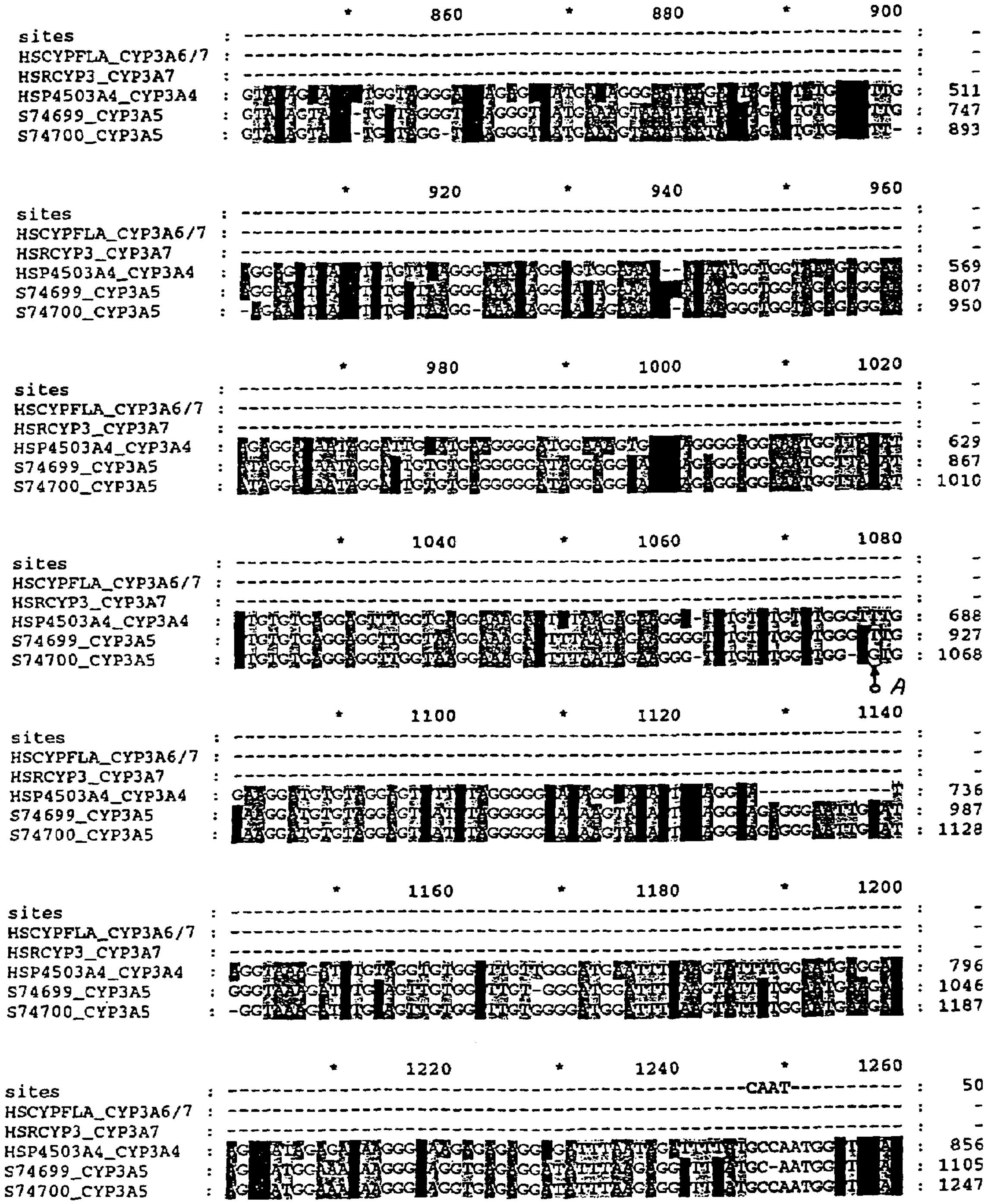

```
                              *         860         *         880         *         900
sites              : ------------------------------------------------------------ : -
HSCYPFLA_CYP3A6/7  : ------------------------------------------------------------ : -
HSRCYP3_CYP3A7     : ------------------------------------------------------------ : -
HSP4503A4_CYP3A4   : [aligned sequence]                                            : 511
S74699_CYP3A5      : [aligned sequence]                                            : 747
S74700_CYP3A5      : [aligned sequence]                                            : 893

                              *         920         *         940         *         960
sites              : ------------------------------------------------------------ : -
HSCYPFLA_CYP3A6/7  : ------------------------------------------------------------ : -
HSRCYP3_CYP3A7     : ------------------------------------------------------------ : -
HSP4503A4_CYP3A4   : [aligned sequence]                                            : 569
S74699_CYP3A5      : [aligned sequence]                                            : 807
S74700_CYP3A5      : [aligned sequence]                                            : 950

                              *         980         *        1000         *        1020
sites              : ------------------------------------------------------------ : -
HSCYPFLA_CYP3A6/7  : ------------------------------------------------------------ : -
HSRCYP3_CYP3A7     : ------------------------------------------------------------ : -
HSP4503A4_CYP3A4   : [aligned sequence]                                            : 629
S74699_CYP3A5      : [aligned sequence]                                            : 867
S74700_CYP3A5      : [aligned sequence]                                            : 1010

                              *        1040         *        1060         *        1080
sites              : ------------------------------------------------------------ : -
HSCYPFLA_CYP3A6/7  : ------------------------------------------------------------ : -
HSRCYP3_CYP3A7     : ------------------------------------------------------------ : -
HSP4503A4_CYP3A4   : [aligned sequence]                                            : 688
S74699_CYP3A5      : [aligned sequence]                                            : 927
S74700_CYP3A5      : [aligned sequence]                                            : 1068
                                                                        ↓ A

                              *        1100         *        1120         *        1140
sites              : ------------------------------------------------------------ : -
HSCYPFLA_CYP3A6/7  : ------------------------------------------------------------ : -
HSRCYP3_CYP3A7     : ------------------------------------------------------------ : -
HSP4503A4_CYP3A4   : [aligned sequence]                                            : 736
S74699_CYP3A5      : [aligned sequence]                                            : 987
S74700_CYP3A5      : [aligned sequence]                                            : 1128

                              *        1160         *        1180         *        1200
sites              : ------------------------------------------------------------ : -
HSCYPFLA_CYP3A6/7  : ------------------------------------------------------------ : -
HSRCYP3_CYP3A7     : ------------------------------------------------------------ : -
HSP4503A4_CYP3A4   : [aligned sequence]                                            : 796
S74699_CYP3A5      : [aligned sequence]                                            : 1046
S74700_CYP3A5      : [aligned sequence]                                            : 1187

                              *        1220         *        1240         *        1260
sites              : ----------------------------------------CAAT---------------- : 50
HSCYPFLA_CYP3A6/7  : ------------------------------------------------------------ : -
HSRCYP3_CYP3A7     : ------------------------------------------------------------ : -
HSP4503A4_CYP3A4   : [aligned sequence]                                            : 856
S74699_CYP3A5      : [aligned sequence]                                            : 1105
S74700_CYP3A5      : [aligned sequence]                                            : 1247
```

FIG. 9a (CONTINUED 3).

CYP3A4, CYP3A5, CYP3A6/7

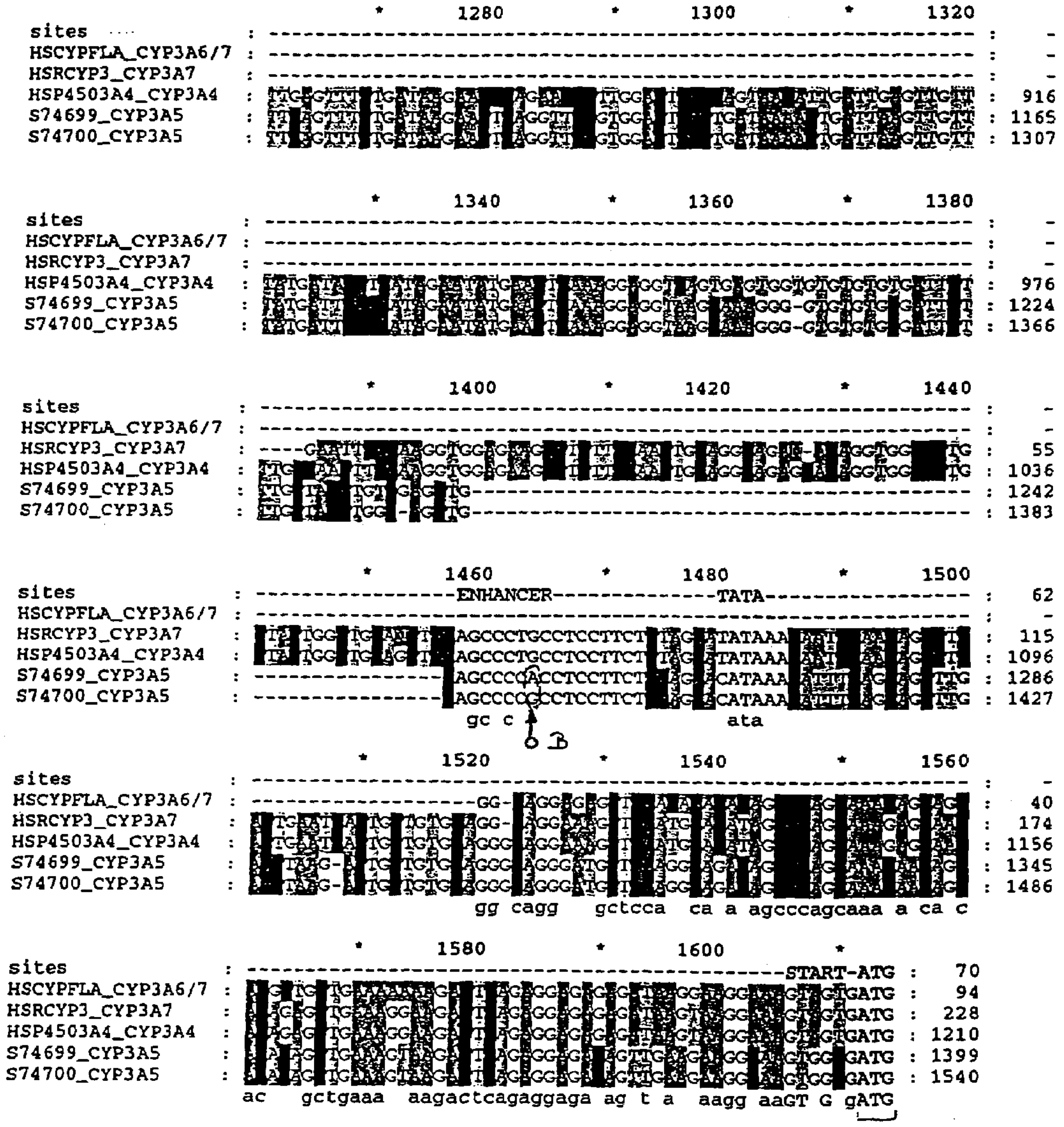

```
                          *         1280         *         1300         *         1320
sites             : ------------------------------------------------------------------  :    -
HSCYPFLA_CYP3A6/7 : ------------------------------------------------------------------  :    -
HSRCYP3_CYP3A7    : ------------------------------------------------------------------  :    -
HSP4503A4_CYP3A4  : [aligned sequence]                                                   :  916
S74699_CYP3A5     : [aligned sequence]                                                   : 1165
S74700_CYP3A5     : [aligned sequence]                                                   : 1307

                          *         1340         *         1360         *         1380
sites             : ------------------------------------------------------------------  :    -
HSCYPFLA_CYP3A6/7 : ------------------------------------------------------------------  :    -
HSRCYP3_CYP3A7    : ------------------------------------------------------------------  :    -
HSP4503A4_CYP3A4  : [aligned sequence]                                                   :  976
S74699_CYP3A5     : [aligned sequence]                                                   : 1224
S74700_CYP3A5     : [aligned sequence]                                                   : 1366

                          *         1400         *         1420         *         1440
sites             : ------------------------------------------------------------------  :    -
HSCYPFLA_CYP3A6/7 : ------------------------------------------------------------------  :    -
HSRCYP3_CYP3A7    : ----G[aligned sequence]                                              :   55
HSP4503A4_CYP3A4  : [aligned sequence]                                                   : 1036
S74699_CYP3A5     : [aligned sequence]--------------------------------                   : 1242
S74700_CYP3A5     : [aligned sequence]--------------------------------                   : 1383

                          *         1460         *         1480         *         1500
sites             : ------------------ENHANCER-------------TATA-------------------       :   62
HSCYPFLA_CYP3A6/7 : ------------------------------------------------------------------  :    -
HSRCYP3_CYP3A7    : [aligned]AGCCCTGCCTCCTTCT[..]TATAAA[..]                              :  115
HSP4503A4_CYP3A4  : [aligned]AGCCCTGCCTCCTTCT[..]TATAAA[..]                              : 1096
S74699_CYP3A5     : ------------AGCCCCACCTCCTTCT[..]CATAAA[..]                           : 1286
S74700_CYP3A5     : ------------AGCCCGCCTCCTTCT[..]CATAAA[..]                            : 1427
                                    gc c                  ata
                                        ↑
                                        b B

                          *         1520         *         1540         *         1560
sites             : ------------------------------------------------------------------  :    -
HSCYPFLA_CYP3A6/7 : -----------------GG-[aligned sequence]                               :   40
HSRCYP3_CYP3A7    : [aligned]GG-[aligned sequence]                                       :  174
HSP4503A4_CYP3A4  : [aligned sequence]                                                   : 1156
S74699_CYP3A5     : [aligned]G-[aligned]GGG[aligned sequence]                            : 1345
S74700_CYP3A5     : [aligned]G-[aligned]GGG[aligned sequence]                            : 1486
                            gg  cagg    gctcca   ca a  agcccagcaaa  a  ca c

                          *         1580         *         1600         *
sites             : ----------------------------------------------START-ATG :   70
HSCYPFLA_CYP3A6/7 : [aligned sequence]GATG                                  :   94
HSRCYP3_CYP3A7    : [aligned sequence]GATG                                  :  228
HSP4503A4_CYP3A4  : [aligned sequence]GATG                                  : 1210
S74699_CYP3A5     : [aligned sequence]GATG                                  : 1399
S74700_CYP3A5     : [aligned sequence]GATG                                  : 1540
                    ac  gctgaaa  aagactcagaggaga  ag t a  aagg aaGT G gATG
```

FIG. 9(b).

```
                A or G
                  =
      MEME repeated motif 9
      =====
            MEME 'single' motif 9
      ===========================
               Yi-consensus
                ==========
        apoE-undefined-site-3
               =========
                ApoE_B1
               =========
           APRT-human_US
              ========
            APRT-CHO_US
              ========
1238  AGCTGCAGCCCCACCTCCTTCTCCAGC   (B) A
      TCGACGTCGGGGTGGAGGAAGAGGTCG
. . . . . . . . . . . . . . . . . . . . . . . . . . . . . . . . . . . . . . . . . . . .
```

FIG. 9(c).

```
       MEME repeated motif 2
          ==============
      MEME repeated motif 2
      ====
             MEME 'single' motif 9
      ===========================
               Yi-consensus
                ==========
               Sp1-TPI_(4)
                  ======
            GCF-consensus
              ==========
                DSE_(1)
             ==========
                  IRE_(1)
                 ========
                Sp1_CS4
               =========
             GC-box_(1)
             ==========
             Sp1-IE-4/5
                 ======
             Sp1-IE-3.3
                 ======
      E2A_CS    hsp70.2
      ======    ======
      E2A_CSSp1-hsp70_(1)
      =====     ======
            APRT-mouse_US
              ========
1379  AGCTGCAGCCCCGCCTCCTTCTCCAGC   (B) G
      TCGACGTCGGGGCGGAGGAAGAGGTCG
. . . . . . . . . . . . . . . . . . . . . . . . . . . . . . . . . . . . . . . . . . . .
```

FIG. 9(d).

```
      MEME repeated motif 9
       ===========
      MEME repeated motif 9
      ========
                MEME repeated motif 3
                              =======
                MEME 'single' motif 6
                      ===============
                         E-2.7_kb_(3)
                                    =
                         E1A-F_CS
                          =======
         GH1            MTVGRE_NRS
      ========            =======
910   TCTGTCTGGCTGGGCTTGCAAGGATGTGTAG    (A) T
      AGACAGACCGACCCGAACGTTCCTACACATC
........................................................
```

FIG. 9(e).

```
      MEME repeated motif 9
           ===========
      MEME repeated motif 9
       ===========
      MEME repeated motif 9
      ========
              MEME repeated motif 3
                            =======
              MEME 'single' motif 6
                    ===============
                       E-2.7_kb_(3)
                                  =
                MBF-I_CS
                 =======
                       E1A-F_CS
                        =======
              CNBP-SREMTVGRE_NRS
              ========  =======
         GH1     MRE_CS2
      ========   =======
1052  TCTGTCTGGCTGGCGTGCAAGGATGTGTAG    (A) G
      AGACAGACCGACCGCACGTTCCTACACATC
........................................................
```

GENOTYPING CYTOCHROME EXPRESSION

FIELD OF THE INVENTION

The present invention is concerned with an assay and, in particular, with an assay for genotyping a polymorphism predictive of a phenotype associated with cytochrome expression, in this case CYP3A5.

BACKGROUND OF THE INVENTION

The cytochrome P450 subfamily CYP3A represents one of the most important families of the P450 superfamily and plays a major role in the metabolism of an ever expanding list of therapeutic compounds (23, 24). This family comprises the most abundantly expressed P450s in human livers, and is responsible for the metabolism of over 50% of all clinically used drugs, including the dihydropyridines, cyclosporin, erythromycin and barbiturates (1). Wide inter-individual variation in the metabolism of CYP3A substrates has been noted and is a factor in determining individual drug efficacy. Evidence also exists for the metabolism of an array of lipophilic environmental pollutants, including the activation of pro-carcinogens such as aflatoxin B1 by members of this subfamily (2).

Presently, four CYP3A cDNAs have been identified in humans, CYP3A3, CYP3A4, CYP3A5 and CYP3A7. It is believed that CYP3A3 represents an allelic variant of CYP3A4, whilst CYP3A4 and CYP3A7 are found only in human adult and fetal livers respectively (3). Initial experiments suggested that a polymorphism existed in CYP3A4 (4). However other studies, whilst confirming a wide range of inter-individual variation in CYP3A4 expression have failed to confirm the original bimodality (5, 6). Overlapping substrate specificities between CYP3A5 and CYP3A5 have previously made it difficult to separate metabolism by these isoforms; consequently little phenotyping data have been produced to study variation in CYP3A5 activity in humans. However, there is evidence for the polymorphic expression of CYP3A5. Use of both immunoblotting and Northern analysis have detected CYP3A5 expression in only 10–30% of human livers (7, 8, 9). More recently, analysis of 30 human liver samples using immunoblotting found that only 3% showed no detectable CYP3A5, whilst a large number had trace amounts, suggesting that a polymorphism in this enzyme may be regulatory as opposed to structural (10). Comparisons of the 5' flanking regions from the CYP3A4, 3A5 and 3A7 genes have identified putative binding sites for several transcriptional regulatory factors common to all isoforms (11, 12, 13). However, the molecular basis, if any, for this inter-individual variation in expression of the CYP3A sub-family members has so far remained unclear. Indeed it has been suggested that the host cellular environment may be a greater determinant of inducibility than gene structure (14). However, the determination of a major genetic component to variant expression and activity, linked to an easy screening method, would be extremely beneficial, not only in providing a predictor of individual response to drugs which are metabolised by these isoforms, but also in facilitating association studies between CYP3A and disease processes.

The delineation of CYP3A4 and CYP3A5 metabolism has been shown to be possible using the sedative midazolam as a probe drug (15). In this case two metabolites are formed, 1-hydroxy midazolam (1-OHM) and 4-hydroxy midazolam (4-OHM). Those samples containing a higher proportion of CYP3A5 compared to CYP3A4 have their metabolism driven towards the 1-OHM route and therefore show a higher ratio of 1-OHM/4-OHM than those containing only CYP3A4. The present inventors have now established that two polymorphisms, located in putative transcriptional regulatory regions, which caused increased CYP3A5 gene expression and metabolic activity are linked and have developed assays for their detection. These assays will allow prediction of inter-individual variability in response to drugs metabolised by this isoform, as well as facilitating disease association studies.

BRIEF DESCRIPTION OF THE FIGURES

The invention may be more clearly understood by the following example with reference to the accompanying drawings wherein

FIG. 2*a*: is a diagram of relative position of primers, and of the recognition site for the restriction enzyme Tai I, which is introduced into the PCR product utilising mismatched primer 3A5R1 when the wild-type "A" nucleotide is present at position −147, and is lost when the mutant "G" nucleotide is present.

FIG. 2*b*: is a diagrammatical representation of expected restriction fragments for each possible genotype for the $A_{-147}G$ variant, i.e. homozygous wild-type, heterozygous and homozygous mutant.

FIG. 2*c*: is an illustration of a 1.5% agarose gel of Tai I restriction digest of 3A5F2/3A5R1 PCR product for detection of the $A_{-147}G$ variant. Lane 1. 100 bp ladder. Lanes 2 & 7. Reference undigested PCR products. Lane 3. Sample homozygous for the wild-type "A" nucleotide at position −147. Lanes 10, 11, 16. Samples heterozygous for the $A_{-147}G$ variant.

FIG. 6: is a list of oligonucleotide mismatch primers (SEQ ID NOS 11–13, respectively in order of appearance) used in accordance with the invention, where the underlined nucleotide indicates the sequence mismatch.

FIG. 7: is an illustration of the nucleotide sequence (SEQ ID NO: 19) of the 5' flanking region relative to the DNA sequence encoding CYP3A5.

FIGS. 9*a*–9*e*: are illustrations of the results obtained from the >find patterns=program of the GCG sequence analysis package (SEQ ID NOS 20–24, respectively in order of appearance in FIG. 9*a*, SEQ ID NO: 25 in FIG. 9(*b*), SEQ ID NO: 26 in FIG. 9(*c*), SEQ ID NO: 27 in FIG. 9(*d*), and SEQ ID NO: 28 in FIG. 9(*e*)).

DETAILED DESCRIPTION OF THE INVENTION

Figure 1A:
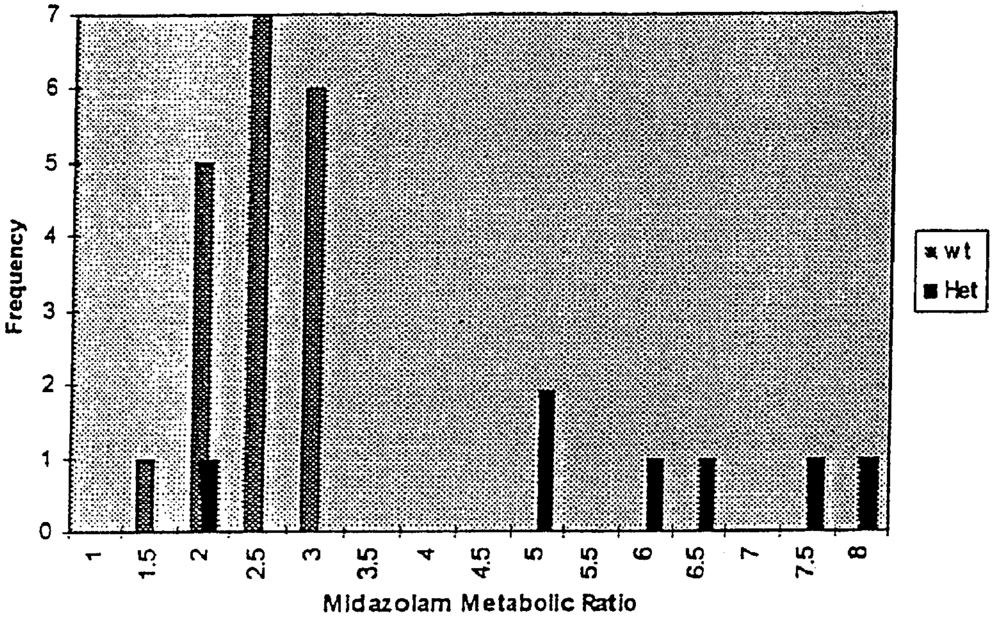
FIG. 1*a*: is an illustration of the relationship between midazolam metabolic ratio and genotype for the linked $A_{-147}G$ and $T_{-475}G$ mutations in the 5' flanking region of the CYP3A5 gene. Midazolam metabolic ratio=1-OHM/4-OHM, wt=samples with the wild type sequence in the 5' flanking region as previously published (11), Het=samples heterozygous for the linked polymorphisms, $A_{-147}G$ and $T_{-475}G$.

Therefore, according to a first aspect of the present invention there is provided a method of identifying subjects having a high or low drug metabolising phenotype associated with cytochrome CYP3A5 expression, which method comprises screening for the presence or absence in the genome of a subject a polymorphic variant in a transcription regulatory region, such as, a promoter or enhancer adjacent the region encoding CYP3A5. Preferably, the method involves screening for a variant in a recognition site for a transcription factor of said regulatory region, and even more preferably in an activator protein-3 motif or a basic transcription element. Even more preferably, the method involves screening for a variant at any one of positions −475 or −147 of the DNA of the 5' flanking region adjacent to the region encoding CYP3A5 the sequence of which flanking region is illustrated in FIG. 7 and preferably, for both the variants at positions −475 and −147.

In one embodiment of the method of the invention genomic DNA is amplified, preferably by the polymerase chain reaction using oligonucleotide molecules capable of hybridising selectively to the wild type sequence or the variant sequences, such that generation of amplified DNA from said molecules will indicate whether said wild type or mutation is present. In this method PCR primers hybridise either to the mutated or wild type sequence, but not both. Amplification of the DNA of the respective mutation or wild type genotype using the respective primers will provide an indication of the presence of the wild type or mutated nucleotide mutations.

A further method of the invention advantageously utilises oligonucleotide molecules as primers which, in addition to hybridising to the site of interest, are capable of introducing a restriction site which is absent in either the wild type sequence or polymorphic variants. Therefore, according to a further aspect of the invention, there is provided a method of identifying subjects having a high or low drug metabolising phenotype associated with CYP 3A5 expression, which method comprises 1) amplifying genomic DNA from a subject using oligonucleotide molecules capable of hybridising to the wild type sequence and/or to the polymorphic variant sequence at a location being analysed, which molecules are such that they can introduce a restriction site at said location which is not present in the wild type or variant sequences, and 2) subjecting amplified DNA from step 1 to a restriction enzyme which cleaves the DNA at said restriction site to provide a restriction digest indicative of the presence or absence of said variant.

The method preferably comprises amplifying DNA in a recognition site for a transcription factor of said regulatory region and preferably in an activator protein-3 motif (AP-3) and/or basic transcription element (BTE). Preferably, the method comprises amplifying DNA spanning any of position −475 or −147, of the regulatory region of CYP 3A5, the sequence of which is illustrated in FIG. 7.

The polymorphisms at the positions identified in each of the methods according to the invention comprise $T_{-475}$ 6 G and $A_{-147}$ 6 G. As presented in the Examples below, the molecule used to detect the variation at $A_{-147}$ 6 G is capable of introducing a restriction site for the enzyme Tai I only when the wild type A nucleotide is present at position −147. Alternatively, the molecule used to detect the $T_{-475}$ 6 G nucleotide variation is capable of introducing a restriction site for the enzyme Alu I only when the wild type T nucleotide is present at position −475.

In this embodiment an example of suitable primers is any of 3A5F1 GGGTCTGTCTGGCTGCGC (SEQ ID NO: 11) and 3A5F2 (GGGGTCTGTCTGGCTGAGC) (SEQ ID NO: 12) and 3A5R1 (TTTATGTGCTGGAGAAGGACG) (SEQ ID NO: 13).

Figure 3:
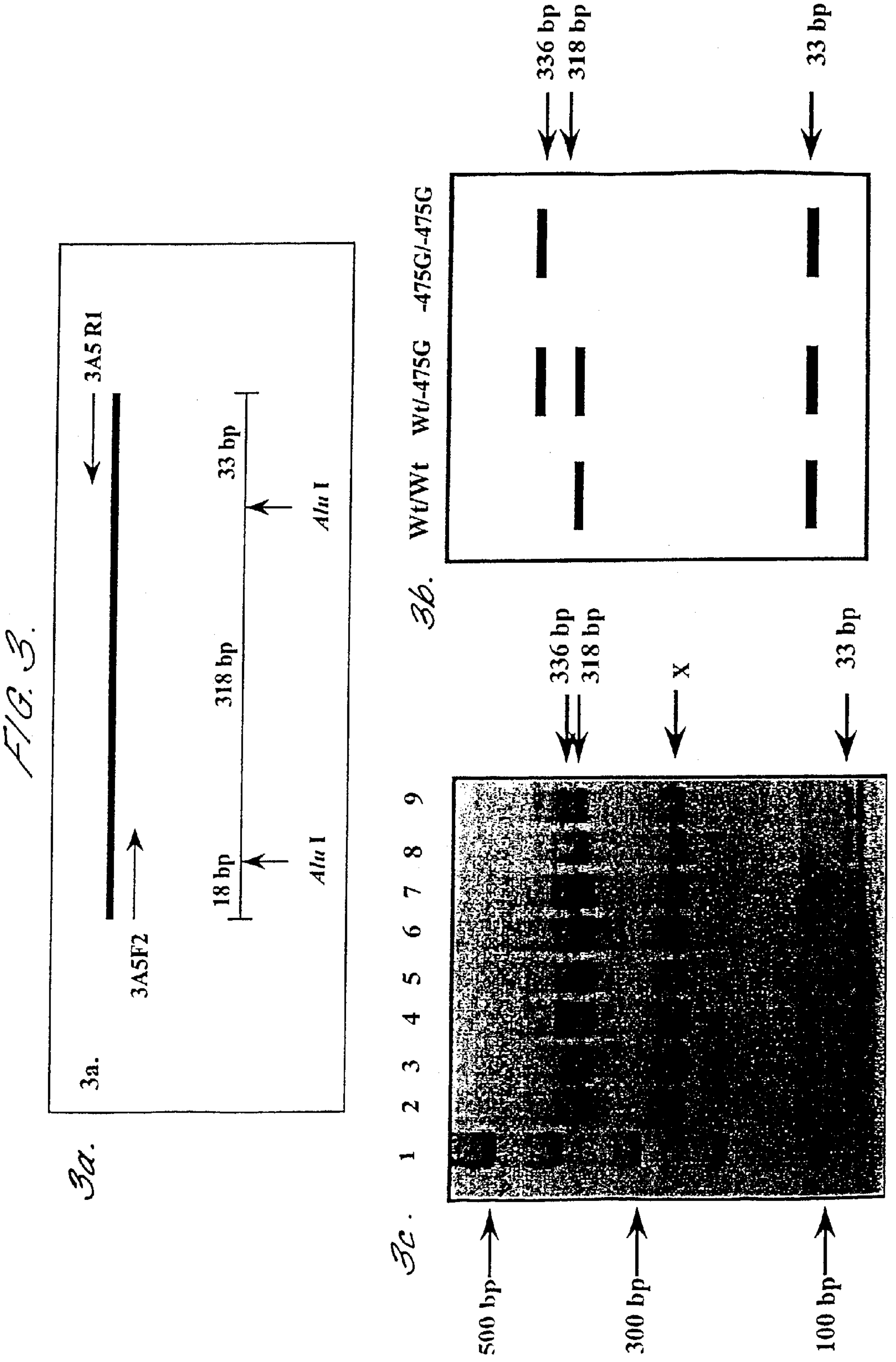
FIG. 3*a*: is a diagram of relative position of primers, and of the recognition sites for the restriction enzyme Alu I. The forward recognition site is introduced into the PCR product utilising mismatched primer 3A5F2 when the wild-type "T" nucleotide is present at position −475, and is lost when the variant "G" nucleotide is present.
FIG. 3*b*: is a diagrammatical representation of expected restriction fragments for each possible genotype for the $T_{-475}G$ variant, i.e. homozygous wild-type, heterozygous and homozygous mutant.
FIG. 3*c*: is an illustration of a 12.5% polyacrylamide ExcelGel of Alu I restriction digest of the 3A5F2/3A5R1 PCR product for detection of the $T_{-475}G$ mutation. Lane 1. 100 bp ladder. Lanes 2, 5, 6, 7 & 8. Samples homozygous for the wild-type AT≅nucleotide at position −147. Lanes 3, 4, 9. Samples heterozygous for the $T_{-475}G$ mutation. Fragment X—additional digestion product resulting from re-amplification of original template by primers 3A51/3A52.

Using oligonucleotide mismatch primer 3A5R1 creates a Tai I recognition site only when the wild type A nucleotide is present at position −147. Digestion of the 369 bp product with Tai I yields fragments of 349 and 20 bp for the wild type sequence, whilst the product remains undigested if a mutant, such as the G nucleotide, is present (FIG. 2). Similarly, for the detection of the $T_{-475}G$ mutation a second oligonucleotide mismatch primer 3AF2 may be used. This primer introduces a recognition site for the restriction enzyme Alu I when the wild type T is present at position −475, digesting the product to yield fragments of 318, 33 and 18 bp. This site is lost when the mutant G nucleotide is present, yielding digestion products of 336 and 33 bp (FIG. 3).

Known techniques for the scoring of single nucleotide polymorphisms (see review by Schafer, A. J. and Hawkins, J. R. in Nature Biotechnology, Vol 16, pp33–39 (1998) include mass spectrometry, particularly matrix-assisted laser desorption/ionization time-of-flight mass spectrometry (MALDI-TOF-MS, se Roskey, M. T. et.al., 1996, PNAS USA, 93: 4724–4729), single nucleotide primer extension (Shumaker, J. M. et.al., 1996, Hum. Mutat., 7: 346–354; Pastinen, T. et.al., 1997, Genome Res., 7: 606–614) and DNA chips or microarrays (Underhill, P. A. et.al., 1996, PNAS USA, 93: 196–200; Gilles, P. N. et.al. Nat. Biotech., 1999, 17: 365–370). The use of DNA chips or microarrays could enable simultaneous genotyping at many different polymorphic loci in a single individual or the simultaneous genotyping of a single polymorphic locus in multiple individuals.

In addition to the above, SNPs are commonly scored using PCR-SSCP based techniques, such as PCR-SSP using allele-specific primers (described by Bunce, 1995). If the SNP results in the abolition or creation of a restriction site then genotyping can be carried out by performing PCR using non-allele specific primers spanning the polymorphic site and digesting the resultant PCR product using the appropriate restriction enzyme. The known techniques for scoring polymorphisms are of general applicability and it would therefore be readily apparent to persons skilled in the art that the known techniques could be adapted for the scoring of single nucleotide polymorphisms in the the regulatory region of CYP 3A5.

As would be readily apparent to those skilled in the art, genotyping is generally carried out on genomic DNA prepared from a suitable tissue sample obtained from the subject under test. Most preferably, genomic DNA is prepared from a blood sample, according to standard procedures which are well known in the art. Also provided by the present invention is an oligonucleotide of at least 10 contiguous nucleotides to detect polymorphic variants in a 5' regulatory region adjacent the sequence encoding cytochrome CYP3A5 associated with a high or low drug metabolising phenotype. The oligonucleotide is capable of hybridising to a region incorporating either a mutated or wild type nucleotide at position −475 or −147 of said flanking region, such that amplification of said positions will or will not proceed from said primer according to whether or not a polymorphic variant occurs at any of said positions.

The oligonucleotide molecules of the invention are preferably from 10 to 50 nucleotides in length, even more preferably from 20–30 nucleotides in length, and may be DNA, RNA or a synthetic nucleic acid, and may be chemically or biochemically modified or may contain non-natural or derivatized nucleotide bases, as will be readily appreciated by those skilled in the art. Possible modifications include, for example, the addition of isotopic or non-isotopic labels, substitution of one or more of the naturally occurring nucleotide bases with an analog, internucleotide modifications such as uncharged linkages (e.g. methyl phosphonates, phosphoamidates, carbamates, etc.) or charged linkages (e.g. phosphorothioates, phosphorodithioates, etc.). Also included are synthetic molecules that mimic polynucleotides in their ability to bind to a designated sequence to form a stable hybrid. Such molecules are known in the art and include, for example, so-called peptide nucleic acids (PNAs) in which peptide linkages substitute for phosphate linkages in the backbone of the molecule. An oligonucleotide molecule according to the invention may be produced according to techniques well known in the art, such as by chemical synthesis or recombinant means.

The oligonucleotide molecules of the invention may be double stranded or single stranded but are preferably single stranded, in which case they may correspond to the sense strand or the antisense strand of the 5' regulatory region of CYP3A5. The oligonucleotides may advantageously be used as probes or as primers to initiate DNA synthesis/DNA amplification. They may also be used in diagnostic kits or the like for detecting the presence of one or more variants alleles of the regulatory region of CYP3A5. These tests generally comprise contacting the probe with a sample of test nucleic acid (usually genomic DNA) under hybridising conditions and detecting for the presence of any duplex or triplex formation between the probe and complementary nucleic acid in the sample. The probes may be anchored to a solid support to facilitate their use in the detection of these variants. Preferably, they are present on an array so that multiple probes can simultaneously hybridize to a single sample of target nucleic acid. The probes can be spotted onto the array or synthesised in situ on the array. (See Lockhart et al., Nature Biotechnology, vol. 14, December 1996 "Expression monitoring by hybridisation to high density oligonucleotide arrays". A single array can contain more than 100, 500 or even 1,000 different probes in discrete locations. Preferably, the oligonucleotides comprise any of the primers 3A5F1, 3A5F2 and 3A5R1 as defined herein.

Also provided is a kit to perform the method according to the invention. Preferably, the kit will comprise an oligonucleotide as described herein and even more preferably the kit will further comprise one or more restriction enzymes capable of distinguishing between wild-type or polymorphic variants as defined herein. Preferably, the restriction enzyme comprises Tai I or Alu I.

According to a further aspect of the invention there is also provided a method of identifying toxic or mutagenic effects of a test compound, such as, a drug, toxin or procarcinogen metabolised by CYP3A5 the method comprising contacting each of a cell having a high drug metabolising phenotype and a cell having a low metabolising phenotype associated with cytochrome CYP3A5 expression, with said test compound and identifying the effects of said compound on each of said high or low drug metabolising phenotype cells or other cells sensitive to said compound. An even further aspect comprises a method of diagnosing susceptibility of an individual to a disease associated with environmental toxins or procarcinogens metabolised by CYP3A5, the method comprising the steps of 1) providing a sample containing DNA, and 2) identifying the presence or absence of a mutation in a transcription regulatory region adjacent to the DNA sequence encoding CYP3A5 using a reagent capable of distinguishing the presence or absence of a nucleotide in said regulatory site. According to this aspect of the invention, the mutation occurs in a recognition site for a transcription factor of said regulatory region and preferably in an activator protein-3 motif (AP-3) and/or a basic transcription element (BTE). Preferably, the mutation occurs at any of positions −475 and −147 of the regulatory region and even more preferably at both positions where the mutation may be $T_{-475}G$ or $A_{-147}G$.

Advantageously, it is also envisaged that the regulatory region of the 5' flanking region can be used to identify or purify transcription factors which bind to the 5' region including the respective polymorphic variants. Thus, according to a further aspect of the invention, there is provided a method of identifying transcription factors capable of binding to a DNA fragment from a transcription regulatory region adjacent DNA encoding cytochrome CYP3A5, said method comprising contacting said DNA fragment including said transcription regulatory region with potential transcription factors and identifying any transcription factor complexed to said DNA fragments.

Using the transcription regulatory fragment it is possible to identify compounds or agents which exhibit or exert their effect on the transcription regulatory region of CYP3A5. Thus, there is provided according to this aspect of the invention a method of identifying compounds acting on a transcription regulatory region adjacent to a DNA sequence encoding CYP3A5, the method comprising transforming a cell with a DNA construct comprising the sequence of said regulatory region, and which regulatory region is operably linked to a sequence encoding a reporter molecule, contacting said cell with a test compound and identifying any expression of said reporter molecule. Preferably, said cell is expressing CYP3A5 or is showing CYP3A5 activity.

Also provided by the invention is a method of purification of transcription factors from a sample which are capable of binding to DNA from a transcription regulatory region adjacent a DNA sequence encoding cytochrome CYP3A5, the method comprising contacting a DNA fragment including said transcriptional regulatory region with a mixture of transcription factors and identifying any complexes of said transcription factors and said fragment.

An even further aspect of the invention comprises a method of providing a measure of activity of a transcription regulatory region adjacent to DNA encoding cytochrome CYP3A5 or alternatively a method of identifying a mutation which alters the activity of the transcription regulatory region the method comprising providing a DNA construct having a sequence encoding a reporter molecule operably linked to a DNA fragment comprising said regulatory region, and introducing said construct into a cell and monitoring for the level of expression of said reporter molecule. When the method is used to identify a variant which alters the activity of the transcription regulatory control region, the method may include the further step of comparing the levels of expression of a wild type and a polymorphic regulatory region as described herein.

According to each of the aspects of the invention, the regulatory region includes a polymorphic variation, preferably in a recognition site for a transcription factor of said regulatory region, and preferably in an activator protein-3 motif (AP-3) and/or a basic transcription element (BTE). In a preferred embodiment the variant occurs at position −475 or −147 of the region flanking the sequence encoding CYP3A5, and which region is illustrated in FIG. 7. Preferably, both the variants are present.

The methods of the present invention will be particularly valuable to establish, prior to treatment with a drug, whether the drug will be effectively metabolised by the patient.

Experimental Procedures

Liver Microsome Preparation

Human liver samples were obtained from kidney transplant donors, and flash-frozen immediately on removal. Human liver microsomes were prepared according to previously described protocols (21), and protein content was determined by the method of Lowry as modified by Miller (22).

Midazolam Hydroxylase Assay

The rates of midazolam overall metabolism and of the formation of 1- and 4-OH-midazolam were determined as follows. Each incubation vessel contained an aliquot of the microsomal suspension (containing 1 mg of microsomal protein) in 1.15% KCl −0.01 M phosphate buffer pH 7.4; 10 Fl of a stock solution of 6 mM midazolam dissolved in DMSO to reach a final midazolam concentration of 60 FM; 500 Fl of a co-factor mixture containing 0.5 mg of glucose-6-phosphate, 0.5 mg of $MgCl_2.6H_2O$, 0.5 units of glucose-6-phosphate dehydrogenase dissolved in 0.5 M Na—K-phosphate buffer, pH 7.4 and a 1.15% KCl −0.01 M phosphate buffer pH 7.4 to bring the incubation volume to 0.9 ml. After a pre-incubation for 5 min at 37 EC, the incubations were started by adding 100 Fl of a solution of 1.25 mg/ml NADP to reach a final concentration of 0.125 mg/ml. Tubes were continuously shaken at 100 oscillations/min in an Heto shaking waterbath. Blank incubates with boiled microsomes were incubated under identical conditions as the control incubates. The incubations were stopped after 30 min by immersing the tubes in dry ice. Samples were stored at ≦−18° C. until analysis. The incubation samples were analysed for unchanged midazolam and for its metabolites 1'- and 4-hydroxymidazolam by HPLC with UV-detection.

HPLC Determination of Midazolam Metabolites

The 1-ml samples of midazolam were thawed and diluted with 1 ml DMSO. Samples were sonicated for 10 min, centrifuged and an aliquot of the supernatant was injected directly onto the HPLC-column. The HPLC apparatus consisted of a Waters 600 MS pump. The samples were injected automatically, using a WISP 717 plus automatic injector. Stainless steel columns (30 cm×4.6 mm i.d.) Were packed with Kromasill 18 (5 Fm) bound phase by a balanced density slurry procedure (Haskel DSTV 122-C pump, $10^7$ Pa). UV-detection at 230 nm was performed using a Waters 996 Diode Array Detector. Elution at 1-ml/min started with a short gradient from 100% 0.1 M ammonium acetate, pH 7.0 (solvent system A) to 50% of solvent system A and 50% of solvent system B containing 1M ammonium acetate pH 7.0, methanol and acetonitrile (10/45/45), over a 1-min period, followed by a second gradient to 100% solvent system B in 15 min. This solvent composition was held for 2 min before equilibration with the starting conditions. The identity of the metabolites of midazolam was confirmed using mass spectroscopy. The conversion of UV-peak areas into ng was performed by a Millennium 2020 CDS system on a calibration curve of midazolam. This calibration curve was made up after injection of known amounts of the drug (0, 1059, 2117, 3176 and 5028 ng) and linear (weighted by 1/x) regression analysis of the corresponding UV-peak areas. The equation of the calibration curve was ng=0.000333×area ($r^2$=0.9997, n=5). The metabolic activity was expressed as pmol metabolite formed/min mg protein, and a metabolic ratio was determined for each sample according to the ratio of 10 HM/40 HM in each sample.

Genomic DNA Preparation

DNA was isolated from frozen liver samples using a QIAmp Tissue Kit (QIAGEN) in accordance with the Manufacturer's instructions.

RNA Preparation

RNA was isolated from the liver samples using a QIAGEN RNAeasy Midi Kit (QIAGEN), according to manufacturers instructions. Twenty μg of RNA was treated with RNAse-free DNAse I (Boehringer Mannheim), for 30 min at 37° C. in 20 mM Tris-HCl, pH 8.0, 100 mM $MgCl_2$. Samples were phenol/chloroform extracted, precipitated and resuspended in 30 μl of TE buffer. Two and a half μg of the treated sample was reverse transcribed for 50 minutes at 42° C. in 1× first strand buffer, 0.01M DTT and 0.5M dNTPs using 0.5 μg of oligo(dt) random primers and 200 units SuperScript II Reverse Transcriptase (GibcoBRL) for use on the ABI Prism 7700 Sequence Detection System (SDS).

Sequencing of the CYP3A5 5' Flanking Region

A 1343 bp 5' flanking region of CYP3A5 was PCR amplified from genomic DNA isolated from liver samples, using primers 3A51 (5'-GGAAGCAACCTACATGTC-CATC) (SEQ ID NO: 1) and 3A52 (5'-ATCGCCACTTGC-CTTCTTC) (SEQ ID NO: 10) based on the published sequence of Jounaidi et al. (11). PCR conditions were 1 cycle of 95 EC for 1 min, 30 cycles of 95 EC for 1 min, 57 EC for 30 sec, 72 EC for 2.5 min, and 1 cycle of 72 EC for 10 min. PCR products were purified using a QIAquick PCR Purification Kit (QIAGEN), sequencing primers were designed (Table 1), and used to directly sequence the PCR product on both sense and antisense strands by cycle sequencing using the ABI BigDye Terminator cycle sequencing kit (Perkin Elmer). Sequencing reactions were analysed on an ABI 377 automated sequencer. Contig sequences were aligned and compared using the Sequence Editor version 1.0.3 software packages (Perkin Elmer) and manually edited for identification of heterozygote positions.

All PCR assays were performed utilising a 1 in 100 dilution of the original 3A51/3A52 PCR product as template, under the following conditions: 1 cycle of 95 EC for 1 min, 30 cycles of 95 EC for 1 min, 55 EC for 30 sec, 72 EC for 1 min, and 1 final cycle of 72 EC for 10 min. All products were sequenced to confirm the identity of the product as CYP3A5. Oligonucleotide mismatched primers utilised in the assays were: 3A5F1 (5'-GGGTCTGTCTG-GCTGCGC) (SEQ ID NO: 11), 3A5F2 (5'-GGGGTCT-GTCTGGCTGAGC) (SEQ ID NO: 12), and 3A5R1 (5'-TTTATGTGCTGGAGAAGGACG) (SEQ ID NO: 13), where positions of mismatches are underlined.

PCR Detection Assays for the $A_{-147}G$ and $T_{-475}G$ Mutations

For the $A_{-147}G$ mutation, PCR was performed using primer pair 3A5F2 and 3A5R1. Twenty μl of PCR product was digested for a minimum of 3 hours at 65° C. using 15 units of Tai I, and the restriction fragments visualised by ethidium bromide staining after electrophoresis on a 1.5% agarose gel.

For the $T_{-475}G$ mutation, PCR was performed using primer pair 3A5F2 and 3A5R1 as described above. Twenty μl of PCR product was digested with 15 units of Alu I for a minimum of 3 hours, and restriction fragments were separated by electrophoresis on a 12.5% ExcelGel on a Pharmacia Multiphor Electrophoresis system (Pharmacia). Fragments were visualised by silver staining in a Hoeffer Automatic Gel Stainder (Pharmacia).

To detect the presence of mutations on the same chromosome, PCR was performed using primers 3A5F1 and 3A5R1. Twenty Fl of PCR product was digested for a minimum of 3 hours at 65° C. using 15 units of Mvn I, and the resulting restriction fragments were visualised by ethidium bromide staining after electrophoresis on a 1.5% agarose gel.

Relative Quantification and Comparison of CYP3A5 RNA

Relative levels of CYP3A5 mRNA were determined by real time PCR using the ABI 7700 SDS (Perkin Elmer). Optimal primers and probes for the detection of CYP3A5 were designed using the PrimerExpress program, and subsequently checked to ensure specificity for CYP3A5. Primers utilised for the quantification PCR were: forward—5'-AAGTGGCGATGGACCTCATC-3' (SEQ ID NO: 14); reverse—5'-GAGGAGCACCAGGCTGACA-3' (SEQ ID NO: 15). The TaqMan probe was labelled with the 5' reporter dye 6-carboxy-flouresine (FAM), and had the sequence 5'-CAAATTTGGCGGTGGAAACCTGGC-3' (SEQ ID NO: 16). Optimal primer/probe ratios and concentrations were determined and the experiments run according to standard protocols for the ABI 7700 Standard Detection System. CYP3A5 mRNA expression for all samples was normalised against the expression of β-actin mRNA. The threshold cycle (Ct) is the PCR cycle number where the ABI 7700 begins to detect an increase in fluorescent signal associated with the linear amplification of PCR product. The Ct value is dependent on the initial amount of template copy. Quantities of CYP3A5 in each sample were determined by averaging the Ct from 3 separate PCR reactions of each sample. Relative differences in Ct between samples were calculated by subtracting the Ct of each sample from the highest Ct within the samples (lowest expression). Since the amount of PCR product doubles with every cycle in the linear range of a PCR the differences in Ct were converted into estimated differences of mRNA quantity between the samples by calculating $2^{\delta ct}$, where δCt is the difference in cycle threshold between two samples.

Negative controls were performed on each run to ensure that no signals were due to DNA contamination. Control samples consisted of RNA samples which had been treated in exactly the same manner as for the quantitative PCR, but without the addition of the reverse transcriptase.

Statistical Analysis

Statistical analysis was performed on the JMP Statistical program version 3.2.2 (SAS Institute Inc.). Metabolic ratio and CYP3A5 mRNA expression data were checked to ensure that they conformed to a normal distribution. CYP3A5 mRNA expression data did not conform to a normal distribution and were ln-transformed, afterwhich the data was normally distributed. Metabolic ratios and expression levels were compared between groups using a t-Test.

Western Blot Analysis

Forty micrograms of microsomal protein prepared from each liver were solubilised in an equal volume of Laemmli sample buffer (Biorad) by four cycles of freezing and boiling for 10 minutes. Samples were loaded onto pre-cast 10% SDS-PAGE Ready Gels (Biorad) and electrophoresed for 1 hour at 180 V. Separated proteins were transferred onto Hybond-P membranes (Amersham) using a Trans-blot SD apparatus (Biorad). Membranes were blocked by an overnight incubation at 4° C. in 1× PBS containing 5% (w:v) nonfat milk and 0.1% (v:v) Tween. Membranes were incubated at ambient temperature for 1 hour in a 1:3000 dilution of specific human CYP3A5 antibody (Gentest) in 1× PBS, 2.5% nonfat milk, then rinsed four times in 1× PBS, 2.5% (w:v) nonfat milk, 0.1% (v:v) Tween. Membranes were incubated at ambient temperature for 1 hour in a 1:5000 dilution of Anti-Rabbit IgG peroxidase conjugate (Sigma) in 1× PBS, 2.5% (w:v) nonfat milk, and rinsed as previously. The membranes were developed using the ECL Plus Western Blotting Detection System (Amersham) according to manufacturer's instructions, and visualised by autoradiography using Kodak X-Omat film (sigma).

EXAMPLE 1

Midazolam Phenotyping

A panel of 39 liver samples was phenotyped for CYP3A5 activity, using the metabolism of midazolam to its 1-OH metabolite as a marker of activity. Human liver microsomal samples containing CYP3A5 in addition to CYP3A4 exhibit a significantly greater ratio of 1-OHM to 4-OHM compared with samples containing only CYP3A4. 1-OHM/4-OHM ratios between 5 and 9 were observed for microsomes containing both CYP3A4 and CYP3A5. Samples containing only CYP3A4 showed 1-OHM/4-OHM ratios <4 (15). Analysis of the CYP3A5 phenotypes in our data set showed a clear bimodal distribution, with 6 samples (15%) having metabolic ratios greater then 5, and the remaining samples having metabolic ratios lying between 1.5 and 3.5 (see FIG. 1*a*). Of the 39 liver samples from which microsomes were prepared for metabolic analysis, sufficient tissue was available for full DNA and RNA analysis for 26, which included 6 samples lying in the higher metabolic ratio range. In addition to these 26 samples microsomes for protein analysis were available for a further 3 samples, all of which had metabolic ratios of <4.

Analysis of CYP3A5 Gene 5' Flanking Region

The 5' flanking region of CYP3A5 was PCR-amplified from genomic DNA of all 26 samples and sequenced in full, as shown in FIG. 7. Alignment showed that the region was well conserved. Only a small number of inter-individual variations were identified in addition to a few variations from the published sequence (Table 2.). All variants detected were heterozygous, and all samples heterozygous for the more frequent $A_{-147}G$ mutation were also heterozygous for the $T_{-475}G$ mutation, suggesting that the two mutations were linked. These two mutations fall within two separate putative regulatory elements, a basic transcription element (BTE: $A_{-147}G$) and an activator protein-3 motif (AP-3: $T_{-475}G$). None of the remaining variants fell within putative regulatory domains.

PCR assays were developed to confirm the presence of the $A_{-147}G$ and $T_{-475}$ mutations individually, and to ascertain if the two mutations were on the same, or on separate chromosomes. The PCR assay for the $A_{-147}G$ mutation was based on the creation of a recognition site for the restriction enzyme Tai I by utilising an oligonucleotide mismatch primer (3A5R1). This primer introduces a Tai I recognition site only when the wild-type "A" nucleotide is present at position −147. Digestion of the 369 bp product with Tai I yields fragments of 349 and 20 bp for the wild-type sequence, whilst the product remains undigested if the mutant "G" nucleotide is present (FIG. 2). Similarly, for the detection of the $T_{-475}G$ mutation a second oligonucleotide mismatch primer was used (3A5F2). This primer introduces a recognition site for the restriction enzyme Alu I when the wild-type T nucleotide is present at position −475, digesting the product to yield fragments of 318, 33 and 18 bp. This site is lost when the mutant G nucleotide is present, yielding digestion products of 336 and 33 bp (FIG. 3).

To determine if the mutations were present on the same chromosome a PCR assay was developed utilising two oligonucleotide mismatch primers (3A5F1 and 3A5R1), both primers introducing recognition sites for the restriction enzyme Mvn I when the mutant nucleotides are present at positions −147 and −475. If the mutations are present on the different chromosomes then the original 369 bp product is digested to yield products of 349/350 bp and 20/19 bp (inseperable by gel electrophoresis), whilst if present on the same chromosome the fragment is digested to yield products of 330 and 20/19 bp (data not shown). In addition to confirming the individual genotypes of the samples as determined by sequencing the two mutations were, in all cases, linked on the chromosome (data not shown).

Figure 4A:
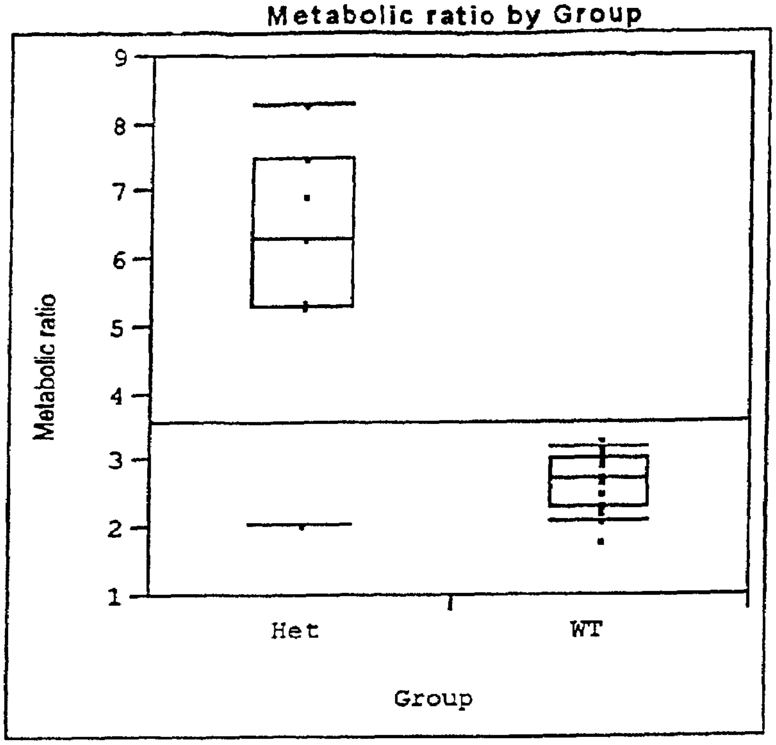
FIG. 4*a*: is a comparison of 1-OHM/4-OHM metabolic ratios between samples with the linked mutations (HET group) and those wild-type for the mutations at positions −147 and −475 (WT group). Mean and quartiles are shown for each group, as is overall mean for the combined groups (central line).

Relationship Between CYP3A5 Allelic Variants, CYP3A5 Mediated Metabolism, CYP3A5 mRNA and Protein Expression Samples were grouped according to genotype: "Wild-type" or "mutant" (containing the linked polymorphisms), and the 1-OHM/4-OHM metabolic ratios (mr) were compared between the groups (FIG. 4*a*). With the exception of one outlier (liver sample number, mr=2.08), all individuals carrying the linked mutations had metabolic ratios >5.0, whilst the wild type group all possessed metabolic ratios of <3.5. The mean metabolic ratios for the mutant group were significantly higher than those from the wild-type group (6.0±2.0 versus 2.7±0.42, mean±standard deviation; $p<0.001$).

Figure 1B:
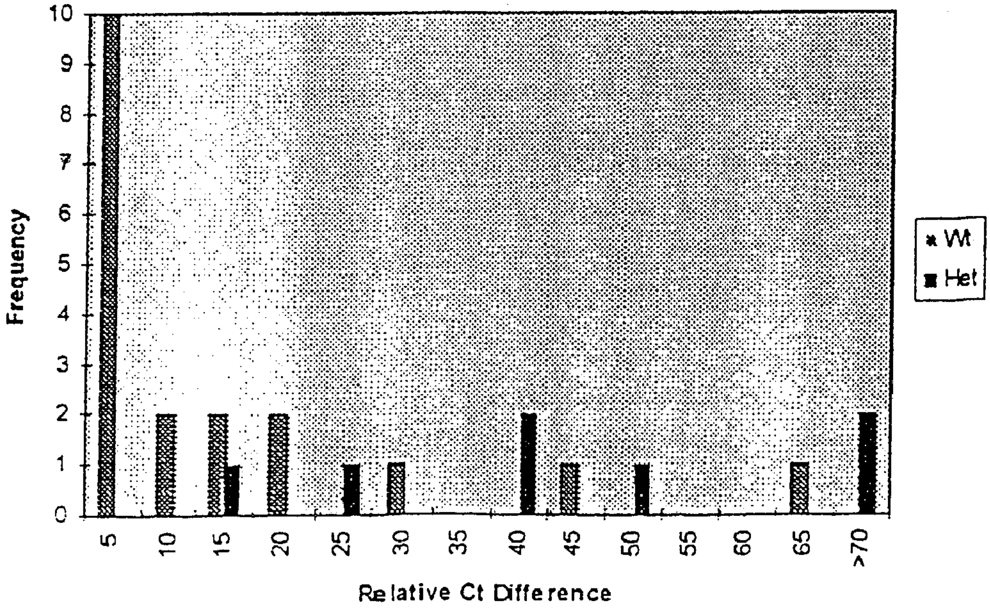
FIG. 1*b*: is an illustration of the relationship between CYP3A5 mRNA expression and the linked $A_{-147}G$ and $T_{-475}G$ mutations in the 5' flanking region of CYP3A5. Relative Ct difference=difference in threshold cycle between samples, as described in the methods section wt=samples with the wild type sequence in the 5' flanking region as previously published (11) Het=samples heterozygous for the linked polymorphisms, $A_{-147}G$ and $T_{-475}G$.
Figure 4B:
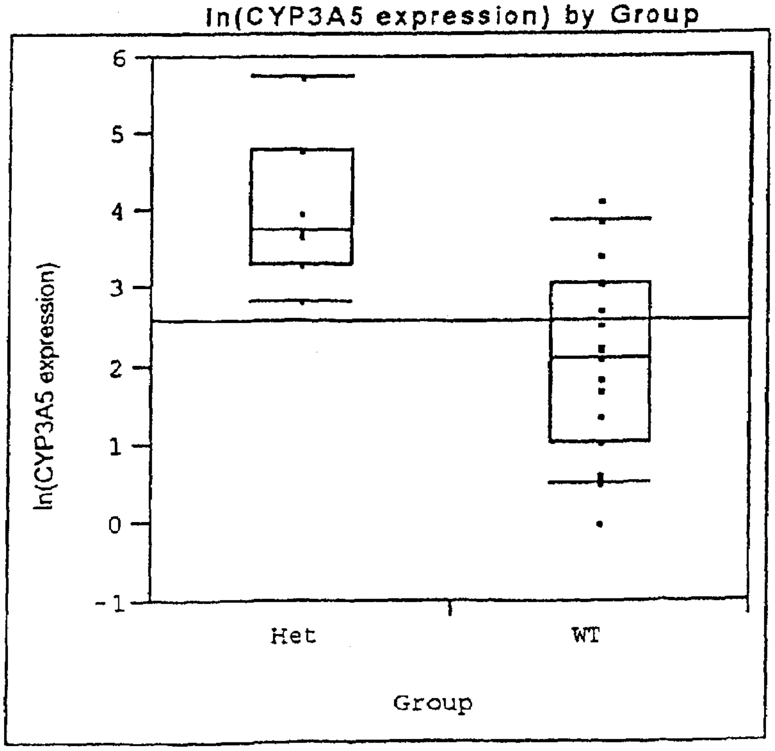
FIG. 4*b*: is a comparison of CYP3A5 expression (ln transformed) between samples with the linked mutations (HET group) and those wild-type for the mutations at positions −147 and −475 (WT group). Mean and quartiles are shown for each group, as is overall mean for the combined groups (central line).

Quantitative PCR was used to ascertain if the mutations in the 5' flanking region were affecting gene expression. Whilst mRNA levels showed greater variation than the metabolic data, a degree of bimodality was observed (FIG. 1*b*). The mutant group had CYP3A5 mRNA levels skewed towards the higher end of the expression range, showing significantly higher levels of CYP3A5 mRNA than the wild type group (mean 1nCt=4.03, standard deviation=0.97, against mean lnCt=2.06, standard deviation=1.2, $p<0.006$) ((FIG. 4*b*). In this case the outlier (presenting with the mutant genotype, but wild type metabolic ratio) also fell within the lower range of expression (lnCt=2.9).

Figure 5:
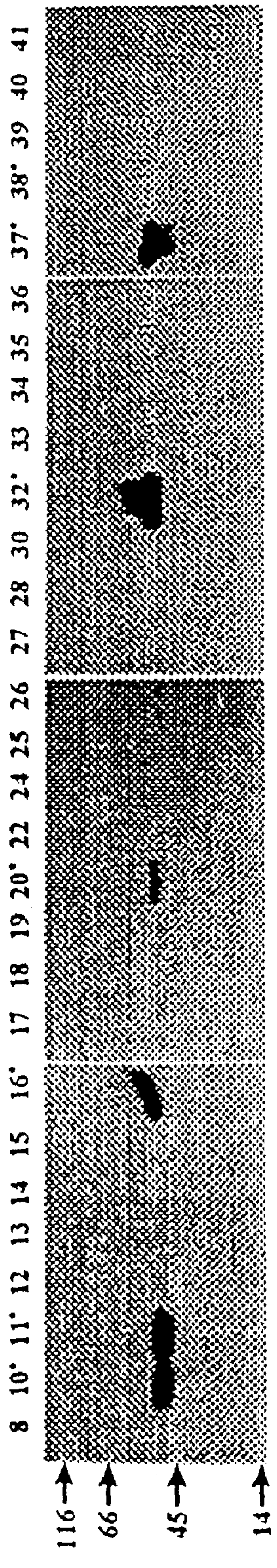
FIG. 5: is a Western blot analysis of CYP3A5 protein expression in liver samples. A Western blot of microsomes prepared from liver samples and probed with a CYP3A5 specific antibody. Liver samples containing the linked polymorphisms at −147 and −475 (wt group) are marked * (sizes indicated in kDa from Wide Range Colour Marker (signs)).

The level of CYP3A5 protein expression levels was determined for 29 liver samples by Western blot analysis using a CYP3A5 specific antibody. A single band of 52 kDa corresponding to CYP3A5 was clearly apparent in some samples. With the exception of the single outlier with the high expression genotype (mutant) and low metabolic ratio phenotype (wild-type), all samples which possessed the high expression genotype, a high metabolic ratio and high RNA expression level clearly show high levels of CYP3A5 expression when compared to those samples with the low expression genotype and phenotype (FIG. 5). The single outlier with the high expression genotype, but low expression phenotype showed levels of CYP3A5 expression similar to those in the low expression genotype group. Longer exposure of the Western blot indicated that a very low level of CYP3A5 expression was apparent in most samples (data not shown).

The 5' flanking sequences of CYP3A5 obtained in this study are virtually identical to those published by Jounaidi et al. (11), and show little inter-individual variation in sequence. Interestingly, Jounaidi et al. sequenced two human genomic clones, one of which contained the two linked mutations described in detail in this report. This would suggest that one clone was derived from an individual in the low expression group, and one from an individual in the high expression/metabolism group.

Previous studies had suggested that CYP3A5 was expressed in 10–30% of livers (7, 8, 9) whilst another study has stated that some expression is constitutive in all samples (10). The present study supports the findings that some CYP3A5 expression is constitutive, with some metabolic activity and mRNA being detected in all livers studied, although CYP3A5 protein was not convincingly demonstrated in all samples using the procedures required. We detected enhanced RNA and protein expression in 23% of the samples for which tissue was available (6 out of 26), which is similar to the fraction of liver showing expression in previous studies. This supports the finding of Boobis et al. (10) that some show low level expression is constitutive in all liver samples although this can only be detected using more sensitive detection techniques (such as PCR, and not by Western or Northern blot analysis).

Whilst both polymorphisms detected lie within putative transcriptional regulatory elements, we suspect that the variant within the BTE is more likely to be responsible for altered expression since it has been reported that a BTE flanking the TATA box accounts for the constitutive expression of CYP1A1, and a similar region has been found in several other CYP genes including CYP2B1, CYP2B2, CYP2E1 (16) CYP3A4 (13) and CYP3A7 (12). In the case of CYP3A4 gene this element has been shown to bind nuclear extracts (13) and a basic transcription element binding factor for CYP3A7 (12), pointing to a role of this region in the general control of cytochrome P450 expression. The exact mechanism of up-regulation of CYP3A5 expression in the allelic variant described here remains to be determined although the presence of one of the mutations within the BTE, and the relevance of this element for the expression of other P450s indicates a possible mechanistic link. Using methylation interference footprinting, it has been shown that all guanine residues within the BTE, and other guanine residues in the vicinity, interacted with the transcriptional factor Sp1 (19). Given that the mutation within the BTE (Sp1) described herein alters an adenine residue to a guanine residue, then this could facilitate binding of transcription factors to the variant form of the Sp1.

Although there is considerable overlap in the range of CYP3A5 mRNA levels seen in the homozygous and heterozygous group, the distribution of metabolic ratios is clearly bimodal, as is the amount of CYP3A5. We cannot exclude the presence of other polymorphisms that may affect the translation efficiency or protein stability of CYP3A5. But given the better correlation between DNA polymorphism and protein level and the notorious liability of RNA, the simpler explanation is that differential RNA degradation or yield (due to differences in sample handling) has blurred the distinction between high and low expressers. Whatever the explanation for the discrepancy at the mRNA level, it does not in any way diminish the predictive value of the DNA polymorphism described.

There is, however, one individual whose genotype (heterozygous mutant) is not predictive of his metabolic phenotype (low expression). The fact that CYP3A5 protein as well as mRNA levels were low in this outlier indicates that the explanation must be sought at the transcriptional level, e.g. in transcription factors controlling CYP3A5 expression.

An AUG element in the 5'-untranslated region of the BTEB gene has been shown to be, at least in part, responsible for cell specific translational control of BTEB (20). Mutations within this region were shown to affect BTEB translation. Therefore, whilst the outlier in our study has a high expression genotype for CYP3A5 expression, this individual may have a "poor" expression phenotype for BTEB. Additionally, it is possible that a mechanism similar to that responsible for inducing CYP1A1 expression may also affect CYP3A5 expression. In addition to the BTE, CYP1A1 expression is mediated by a xenobiotic responsive element (XRE). In this case inducers enhance expression by binding to a cytosolic receptor (Ah receptor) which is translocated into the nucleus (possibly in association with an accessory protein coded for at the Arnt gene), where it binds the XRE (17, 18). Although variations in these and other transcription factors could further modulate CYP3A5 expression, this does not detract from the fact that the polymorphism described here seems to be the major determinant of CYP3A5 expression, at least in liver.

Despite the relatively small number of samples available for analysis in the present study, strong associations have been found between the two linked polymorphisms on the one hand and both expression and CYP3A5 mRNA, protein and activity levels in the liver on the other hand. The unravelling of a genetic mechanism for the polymorphic metabolism by CYP3A5 will have important consequences in the field of pharmacogenetics. The ability to predict metabolism by genotyping will greatly facilitate disease association studies and may also help to explain adverse reactions or poor response to therapeutics which are metabolised by this cytochrome P450 isoform. It will also help in delineating which factors affecting CYP3A5 activity are genetic and which are environmental; for both further work will be required to fully understand the complex variation in expression observed with this enzyme.

Putative Promoter Sequence Analysis

Materials and Methods:

The sequence of the regulatory region of CYP3A5 was analyzed with the 'findpatterns' program of the GCG sequence analysis package (GCG, Madison, Wis.). This program finds specific DNA sequence motifs, patterns, and transcription binding sites, whose sequences are stored in the program, and are present in the sequence of interest. In the present analysis, at most one single mismatch or error per pattern is allowed in the sequence of interest, to detect if the two reported variations alter any known motifs or transcription binding sites. Results are identified in FIGS. 9*a* to 9*e*.

The first, GCGTG to GCTTG variation removes binding sites for MBF-I_CS, MRE_CS2, and CNBP-SRE.

The second, CCACC to CCGCC variation replaces binding sites for apoE-undefined-site-3, ApoE_B1, APRT-CHO_US, and APRT-human_US by GCF-consensus, APRT-mouse_US, GC-box_(1), DSE_(1), Sp1_CS4, Sp1-hsp70_(1), hsp70.2, Sp1-IE-3.3, Sp1-IE-4/5, IRE_(1), Sp1-TPI_(4) does not affect the Yi-consensus pattern Both mutations affect transcription factor binding sites.

Electrophoretic Mobility Shift Assay (EMSA)

An EMSA was carried out using the Sp1 NUSHIFT Kit from Geneka Biotechnology Inc. (Montreal, Canada) according to the manufactures instructions. Briefly, a 31-mer double-stranded oligonucleotide corresponding to the CYP3A5 5'-untranslated region containing the $A_{-147}G$ polymorphism (5'-GGC AGC TGC AGC CCC GCC TCC TTC TCC AGC A-3') (SEQ ID NO: 17) was end-labeled with $^{32}$-P using T4 polynucleotide kinase. 50,000 cpm (0.5 ng) oligonucleotide was incubated with 2 μg HeLa nuclear extract for 30 min at 16° C. Unlabeled mutant or wildtype (5'-GGC AGC TGC AGC CCC ACC TCC TTC TCC AGC A-3') (SEQ ID NO: 18) oligo nucleotide was added in 50-fold or 100-fold excess as indicated. 1 or 2 μl anti-Sp1 rabbit polyclonal antibody was pre-incubated with the nuclear extract at 4° C. for 30 min as indicated. Nuclear extract, anti-Sp1 antibody and binding buffers were from Geneka Biotechnology Inc. Samples were separated on a 5% polyacrylamide (39:1) gel, in TGE buffer (25 mM Tris, 190 mM glycine, 1 mM EDTA, pH 8.3). The dried gel was exposed to X-ray film.

Results

Figure 8:
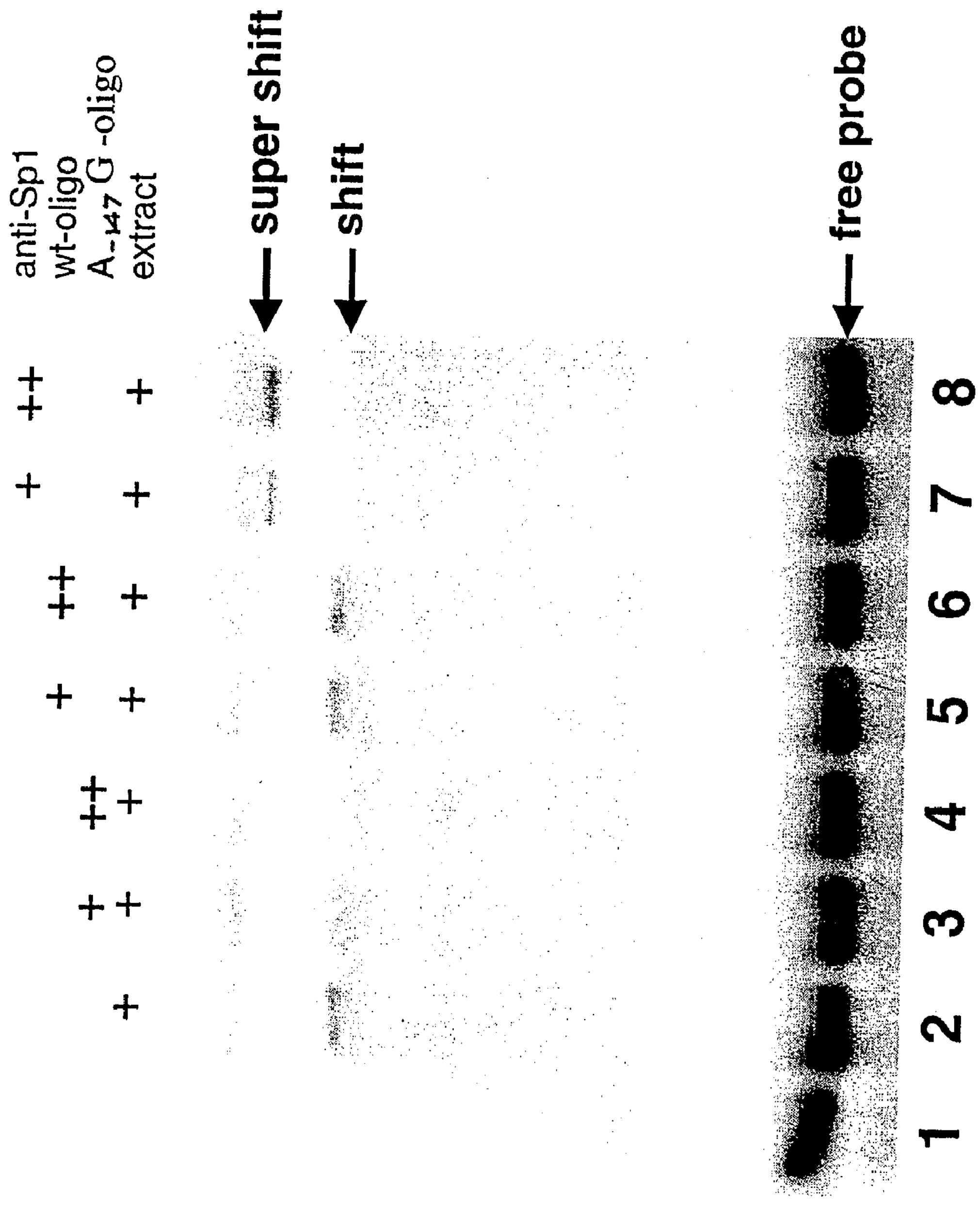
FIG. 8: is an illustration of the results obtained from an Electrophoretic mobility shift assay (EMSA) of $A_{-147}G$ oligonucleotide. EMSA was carried out as described in materials and methods. Lane 1: A-147G oligonucleotide without HeLa nuclear extract; lanes 2–8: in the presence of HeLa nuclear extract; lanes 3 and 4: in the presence of 50–100 fold molar excess of unlabeled A-147G oligonucleotide; lanes 5 and 6; in the presence of 50–100 fold molar excess of unlabeled wild type oligonucleotide; lanes 7 and 8: in the presence of 1 and 2 microlitres of anti-Sp1 antibody.

Analysis of the 5'-untranslated region of the CYP3A5 gene indicated that the $A_{-147}G$ polymorphism might create a binding site for the transcription factor Sp1. An electrophoretic mobility shift assay (EMSA) was carried out to test this hypothesis. An oligo nucleotide containing the $A_{-147}G$ polymorphism was used to assay for binding factors present in HeLa nuclear extracts. A band shift was observed (FIG. 8, lane 2) which was competed away with 50- and 100-fold excess respectively of unlabeled oligo nucleotide (FIG. 8, lanes 3 and 4), but not with wildtype oligo nucleotide (FIG. 8, lanes 5 and 6). This clearly indicates the presence of a protein factor in HeLa nuclear extracts capable of binding to the $A_{-147}G$ polymorphism region, but not to the wildtype region. Incubations in the presence of an antibody specific for the transcription factor Sp1 resulted in supershifting of the $A_{-147}G$ polymorphism oligo nucleotide (FIG. 8, lanes 7 and 8), indicting that Sp1 is binding to the $A_{-147}G$ polymorphism site.

This change in binding affinity of transcription factor Sp1 to the 5'-untranslated region of the CYP3A5 gene might account for the increase in transcription from the $A_{-147}G$ polymorphic promoter and in turn, might contribute to the increase in metabolic rates correlated with the $A_{-147}G$ polymorphisms.

Genotyping of the Cytochrome Expression

A group of 300 healthy Caucasian volunteers was genotyped for variations $T_{-475}$>G and $A_{-147}$>G of the cytochrome P450 3A5 gene.

Test Rationale

The first objective concerned allele/genotype frequencies.

Because the initial study included only 30 to 35 different individuals, allele/genotype frequencies could not be determined. Genotyping a group of 300 subjects should permit determination of these frequencies and to check whether they are in agreement with the Hardy-Weinberg equilibrium.

The second objective concerned the linkage of the two variations. In the initial study, all samples with the gene variations $T_{-475}$>G and $A_{-147}$>G (only 6 in total) were linked. To verify the suggested linkage, both of these CYP 3A5 polymorphisms were genotyped on a larger population.

Materials and Methods

In order to minimize genotyping errors, genomic DNA samples from 300 healthy Caucasian volunteers were genotyped in a microtiterplate based format, which ensured a blind and completely independent duplicate analysis of each individual sample.

A 1343 bp 5' flanking region of CYP3A5 was PCR-amplified from genomic DNA using primers 3A51/3A52. PCR assays for both variations were performed using a 1/100 dilution of the original 3A51/3A52 PCR product as template. Mismatch primers 3A5F2 and 3A5R1 were utilised for both assays. For the $A_{-147}$>G mutation the PCR product was digested with restriction enzyme Tai I, and for the $T_{-475}$>G mutation the PCR product was digested with restriction enzyme Alu I. After digestion the restriction fragments were separated by polyacrylamide gel electrophoresis and visualised by silver staining. The genotypes were determined based on the DNA fragment patterns by two independent observers.

Results

1. Allele/Genotype Frequencies

In the population of 300 individuals, 53 heterozygous subjects (18%) were carrying one copy of each of the variations, 246 subjects (82%) were homogenious for $A_{-147}$ and $T_{-475}$, and one individual (0.3%) was carrying variations $G_{-147}$ and $G_{-475}$ on both allelles (homozygous). These frequencies are in agreement with 3A5 expression found in previous studies (7,8,9)

The allele frequencies are in agreement with the Hardy-Weinberg equilibrium (Table 3).

2. Linkage of Variations $T_{-475}$>G and $A_{-147}$>G

In all individuals, respectively variations $T_{-475}$ and $A_{-147}$, and variations $G_{-475}$, and $G_{-147}$, were equally represented in genotypes, indicating a strong linkage between both variations. Whether this linkage between both variations has some functional significance needs to be clarified further. As a consequence of the linkage, future genotyping will require only the analysis of one of the variations, whether it is the functional variant or not.

REFERENCES

1. Cholerton, S., Daley, A. K., Idle, J. R., The role of individual human cytochrome P450 in drug metabolism and clinical response. *Trend Pharmac. Sci.* 13, 434–439 (1992).
2. Shimada, T., Guengerich, F. P. Evidence for cytochrome P-450NF, the nifedipine oxidase, being the principal enzyme involved in the bioactivation of aflatoxins in human liver. *J. Biol. Chem.* 86, 462–465 (1989).
3. Kormori M. et al. Fetus specific expression of a form of cytochrome P-450 in human livers. *Biochemistry* 29, 4430–4433 (1990).
4. Hoyo-Vadillo, C. et al. Pharmacokinetics of nifedipine slow release tablets in Mexican patients: further evidence for an oxidative polymorphism. *J. Clin. Pharmac.* 29, 816–820 (1989).
5. Renwick, A. G., Robertson, D. R. C., Macklin, B., Challenor, V., Waller, D. G., George, C. F. The pharmacokinetics of oral nifedipine—a population study. *Br. J. Clin. Pharmcol.* 25, 701–708 (1988).
6. Schellens, J. H. M., Soons, P. A., Breimer, D. D. Lack of nifedipine plasma kinetics in a large population of healthy subjects. *Biochem. Pharmacol.* 37, 2507–2510 (1988).
7. Aoyama, T., et al., Cytochrome P450 hPCN3 a novel cytochrome P450IIIA gene product that is differentially expressed in adult human liver. *J. Biol. Chem.* 264, 10388–10395 (1989).
8. Wrighton, S. A. et al. Studies in the expression and metabolic capabilities of human liver cytochrome P450IIIA5 (HLp3). *Mol. Pharmacol.* 38, 207–213 (1990).
9. Schuetz, J., Beach, P., Guzelian, P. S. Selective expression of cytochrome P450 CYP3A mRNAs in embryonic and adult human liver. *Pharmacogenetics,* 4, 11–20 (1994).
10. Boobis A. R., Edwards, R. J., Adams, D. A., Davies, D. S. Dissecting the function of cytochrome P450. *Br. J. Clin. Pharmacol.* 42: 81–89 (1996).
11. Jounaidi, Y., Guzelina, P. S., Maurel, P., Vilarem, M. J. Sequence of the 5'-flanking region of CYP3A5 comparative analysis with CYP3A4 and CYP3A7. *Biochem. Biophys. Res. Commun.* 3, 1741–1747 (1994).
12. Itoh, S., et al. Genomic organisation of human fetal specific P-450IIA7 (cytochrome P-450HFLa)—related gene(s) and interaction of transcriptional regulatory factor with its DNA element in the 5' flanking region. *Biochemica et Biophysia Acta.* 1130, 133–138 (1992).
13. Hashimoto, H., et al. Gene structure of CYP3A4, an adult specific form of cytochrome P450 in human livers and its transcriptional regulation. *Eur. J. Biochem.* 218, 585–595 (1993).

14. Barwick J L., Quattrochi, L. C., Mills, A. S., Potenza, C., Tukey, Guzelian, P. S. Trans-species gene transfer for analysis of glucocorticoid-inducible trancriptional activation of transiently expressed human CYP3A4 and rabbit CY{3A6 in primary cultures of adult rat and rabbit hepatocytes. *Molecular Pharmacology,* 50, 10–16 (1996).

15. Gorski, J. C., Hall, S. D., Jones, D. R., VandenBranden, M., Wrighton, S. A. Regioselective biotransformation of midazolam by members of the human cytochrome P450 (CYP3A) subfamily. *Biochem. Pharmacol.* 9, 1643–1653 (1994).

16. Fujii-Kuriyama, Y., Imataka, H., Sogawa, K., Yasumoto, K. I., Kikuchi, Y. Regulation of CYP1A1 expression. *FASEB J.* 6, 706–710 (1992).

17. Nebert, D. W. The Ah locus: genetic differences in toxicity, Cancer, mutation and birth defects. *Critical Reviews in Toxicology,* 20, 153–174 (1989).

18. Hoffman, E. C., et al. Cloning of a factor required for activity of the Ah (dioxin) receptor. *Science,* 252, 954–958 (1991).

19. Sogawa, K., Kikuchi, Y., Imataka, H., Fujii-Kuriyama Y. Comparison of DNA-binding properties between BTEB and Sp 1. *J. Biochem,* 114, 605–9 (1993).

20. Imataka, H., Nakayama, K., Yasumoto, K., Mizuno, A., Fujii-Kuriyama, Y., Hayami M. Cell specific translational control of transcription factor BTEB expression. The role of an upstream AUG in the 5' untranslated region. *J. Biol. Chem.* 269, 20668–73 (1994).

21. Lavrijsen K., Van Houdt, J., Thijs, D., Meuldermans, W., Heykants, J. Induction potential of antifungals containing an imidazole or triazole moiety. Miconazole and ketoconazole, but not itraconazole are able to induce hepatic drug metabolising enzymes of male rats at high doses. *Biochem. Pharmacol.* 35, 1867–78 (1986).

22. Miller, G. L. Protein determination for large numbers of samples. *Anal. Chem.* 31, 964 (1959).

23. Guengerich, F. P. Characterisation of human cytochrome P450 enzymes. *FASEB* 6, 745–748 (1992).

24. Watkins, P. B. Drug metabolism by cytochromes P450 in the liver and small bowel. *Gastroenterology Clinics of North America,* 21, 511–526 (1992).

25. Haehner, B. D. et al. Bimodal distribution of renal cytochrome P450 3A activity in humans. *Mol. Pharmacol.,* 50, 52–59 (1996).

TABLE 1

Primers used for sequencing 5' flanking region of CYP3A5 from PCR product 3A51/3A52 (see text).

| Primer | Orientation # | Position* | Sequence (5'-3') |
|---|---|---|---|
| 3A51 | F | −12376 −1217 | GGAAGCAACCTACATGTCCATC (SEQ ID NO: 1) |
| 3A5p01 | F | −9786 −963 | AGTACAGGGAGCACAG (SEQ ID NO: 2) |
| 3A5p08 | R | −9176 −932 | CACCTATTCATTCCTG (SEQ ID NO: 3) |
| 3A5p02 | F | −6986 −684 | TGCTATCACCACAGAC (SEQ ID NO: 4) |
| 3A5p07 | R | −6896 704 | GGTGATAGCAATAGAC (SEQ ID NO: 5) |
| 3A5p03 | F | −3646 −349 | AGGATGTGTAGGAGTC (SEQ ID NO: 6) |
| 3A5p06 | R | −4176 −434 | CCTCACACAGATGTAACC (SEQ ID NO: 7) |
| 3A5p04 | F | −1766 −161 | TAAGAACTCAGGTTCC (SEQ ID NO: 8) |
| 3A5p05 | R | −1786 −194 | CAGAAACTGAAGTGGAG (SEQ ID NO: 9) |
| 3A52 | R | +1056 +87 | ATCGCCACTTGCCTTCTTC (SEQ ID NO: 10) |

#F = 5' to 3', R = 3' to 5'
*Primer locations are based on CYP3A5 sequence data of Jounaidi et al (11)

TABLE 2

| Position | Variant Sequence | Percentage |
|---|---|---|
| −475 | T-K (T or G) heterozygote | 30.6% (11/36) |
| −147 | A-R (A or G) heterozygote | 30.6% (11/36) |

TABLE 3

Hardy Weinberg Equilibrium test — Test: CYP3A5-45 A>G; Population: CON-JRF-1

| | Observed values | | Expected values | |
|---|---|---|---|---|
| | N | freq | N | freq |
| genotype AA | 246 | 0.820 | 247.5 | 0.825 |
| genotype AG | 53 | 0.177 | 50.0 | 0.167 |
| genotype GG | 1 | 0.003 | 2.5 | 0.008 |
| total | 300 | 1 | 300 | 1 |

1.112 = Chi-square (Pearson)
0.292 = p-value
1 = d.f.

| | N | freq |
|---|---|---|
| Allele A | 545 | 0.908 |
| Allele G | 55 | 0.092 |

The invention claimed is:

1. A method of identifying the drug metabolizing phenotype of a subject as high or low, wherein said phenotype is associated with cytochrome CYP3A5 expression from variant or wild-type DNA sequences, which method comprises the steps of:

obtaining from the subject a sample comprising genomic DNA;

screening the genomic DNA from said sample for the presence or absence of both variants $T_{-475}G$ and $A_{-147}G$ in the transcriptional regulatory region of CYP3A5; and identifying the subject as having a high drug metabolizing phenotype if both variants are present, or identifying the subject as having a low drug metabolizing phenotype if both variants are absent.

2. The method according to claim 1, wherein during said screening the genomic DNA is amplified using oligonucleotide molecules that hybridize selectively to wild-type or variant DNA sequences, such that generation of amplified DNA indicates whether said variants are present or absent.

* * * * *

SEQUENCE LISTING

<160> NUMBER OF SEQ ID NOS: 28

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ggaagcaacc tacatgtcca tc 22

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
agtacaggga gcacag 16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
cacctattca ttcctg 16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
tgctatcacc acagac 16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
ggtgatagca atagac 16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 6

-continued

```
aggatgtgta ggagtc                                                    16


<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

cctcacacag atgtaacc                                                  18


<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

taagaactca ggttcc                                                    16


<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

cagaaactga agtggag                                                   17


<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

atcgccactt gccttcttc                                                 19


<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

gggtctgtct ggctgcgc                                                  18


<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

-continued ggggtctgtc tggctgagc 19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tttatgtgct ggagaaggac g 21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
aagtggcgat ggacctcatc 20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gaggagcacc aggctgaca 19

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
caaatttggc ggtggaaacc tggc 24

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
ggcagctgca gccccgcctc cttctccagc a 31

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
ggcagctgca gccccacctc cttctccagc a 31

-continued

<210> SEQ ID NO 19
<211> LENGTH: 1346
<212> TYPE: DNA
<213> ORGANISM: Homo sapiens

<400> SEQUENCE: 19
ggaagcaacc tacatgtcca tcaacagatg aatgggtaaa gagagtactt cacttatgca 60
caatggagta caattcagcc atgaaaaaag catgagatcc tgtcctttat aataacgtgg 120
ctggaactgc aggtcattat gttaggtaaa ataagccagg cacacaaaga cagacattgc 180
atgttctcac ttatttgtgg gatctacaaa tcaaaacaat tgagctaatg tctgggtctt 240
agtcaatttt gtaccctaag tacagggagc acagccatta gaatacatga tgaatgcttt 300
aatacaggaa tgaataggtg agaggcacag ggtggttggg tgttcttctg atacatagta 360
tcttccttga cacattcagt acaactctca acaggtaagt ctcttcatgt atgttacctt 420
ctgaggaatt aagtggcaga acatgccttc tattattttc ctttgcagaa caagaccaat 480
tgcattagtt gggaaacagt gctggctgca tctgagcccc aagcaaccat tagtctattg 540
ctatcaccac agactcagag gggatgacac acaggggccc agcaatctca cccaagtcaa 600
ctccaccaac atttctggtc acccaccatg tgtacagtac cctgctaggg tccagggtca 660
tgaaagtaaa taataccaga ctgtgccctt gaggaactca cctctgctaa gggaaacagg 720
cacagaaacc cacaagggtg gtagagagga aataggacaa taggactgtg tgagggggat 780
aggaggcacc cagaggagga aatggttaca tctgtgtgag gaggttggta aggaaagact 840
ttaatagaag ggtctgtct ggctgggctt gcaaggatgt gtaggagtca tctaggggc 900 acaagtacac tccaggcaga gggaattgca tgggtaaaga tctgcagttg tggcttgtgg 960
ggatggattt caagtattct ggaatgaaga cagccatgga aacaagggca ggtgagagga 1020
tatttaagag gcttcatgcc aatggctcca cttcagtttc tgataagaac tcaggttccg 1080
tggactccct gataaaactg attaagttgt ttatgattcc ccatagaata tgaactcaaa 1140
ggaggtaagc aaaggggtgt gtgcgattct ttgctactgg ctgcagctgc agccccacct 1200
ccttctccag cacataaaca tttcagcagc ttgacctaag actgctgtgc agggcaggga 1260
tgctccaggc agacagccca gcaaacaaca gcacacagct gaaagtaaga ctcagaggag 1320
acagttgaag aaggcaagtg gcgatg 1346

<210> SEQ ID NO 20
<211> LENGTH: 94
<212> TYPE: DNA
<213> ORGANISM: Homo sapiens

<400> SEQUENCE: 20
ggcaggagag ctccacacac acagcccagc aaacagcagc acgctgctga aaaaaagact 60
cagaggagag agataaggaa ggaaagtagt gatg 94

<210> SEQ ID NO 21
<211> LENGTH: 228
<212> TYPE: DNA
<213> ORGANISM: Homo sapiens
<220> FEATURE:
<221> NAME/KEY: modified_base
<222> LOCATION: (42)
<223> OTHER INFORMATION: a, c, g, t, other or unknown
<220> FEATURE:
<221> NAME/KEY: modified_base
<222> LOCATION: (68)

-continued

<223> OTHER INFORMATION: a, c, g, t, other or unknown

<400> SEQUENCE: 21

```
gaattcccaa ggtggagaag cctcttccaa ctgcaggcag anacaggtgg ccctgctact     60

ggctgcanct ccagccctgc ctccttctct agcatataaa caatccaaca gcctcactga    120

atcactgctg tgcaggcagg aaagctccat gcacatagcc cagcaaagag caacacagag    180

ctgaaaggaa gactcagagg agagagataa gtaaggaaag tagtgatg                 228
```

<210> SEQ ID NO 22
<211> LENGTH: 1210
<212> TYPE: DNA
<213> ORGANISM: Homo sapiens

<400> SEQUENCE: 22

```
ctgcagtgac cactgcccca tcattgctgg ctgaggtggt tggggtccat ctggctatct     60

gggcagctgt tctcttctct cctttctctc ctgtttccag acatgcagta tttccagaga    120

gaaggggcca ctctttggca aagaacctgt ctaacttgct atctatggca ggacctttga    180

agggttcaca ggaagcagca caaattgata ctattccacc aagccatcag ctccatctca    240

tccatgccct gtctctcctt taggggtccc cttgccaaca gaatcacaga ggaccagcct    300

gaaagtgcag agacagcagc tgaggcacag ccaagagctc tggctgtatt aatgacctaa    360

gaagtcacca gaaagtcaga aggatgcata gcagaggccc agcaatctca gctaagtcaa    420

ctccaccagc ctttctagtt gcccactgtg tgtacagcac cctggtaggg accagagcca    480

tgacagggaa taagactaga ctatgccctt gaggagctca cctctgttca gggaaacagg    540

cgtggaaaca caatggtggt aaagaggaaa gaggacaata ggattgcatg aaggggatgg    600

aaagtgccca ggggaggaaa tggttacatc tgtgtgagga gtttggtgag gaaagactct    660

aagagaaggc tctgtctgtc tgggtttgga aggatgtgta ggagtcttct agggggcaca    720

ggcacactcc aggcataggt aaagatctgt aggtgtggct tgttgggatg aatttcaagt    780

attttggaat gaggacagcc atagagacaa gggcaagaga gaggcgattt aatagatttt    840

atgccaatgg ctccacttga gtttctgata agaacccaga acccttggac tccccagtaa    900

cattgattga gttgtttatg atacctcata gaatatgaac tcaaaggagg tcagtgagtg    960

gtgtgtgtgt gattctttgc caacttccaa ggtggagaag cctcttccaa ctgcaggcag   1020

agcacaggtg gccctgctac tggctgcagc tccagccctg cctccttctc tagcatataa   1080

acaatccaac agcctcactg aatcactgct gtgcagggca ggaaagctcc atgcacatag   1140

cccagcaaag agcaacacag agctgaaagg aagactcaga ggagagagat aagtaaggaa   1200

agtagtgatg                                                          1210
```

<210> SEQ ID NO 23
<211> LENGTH: 1399
<212> TYPE: DNA
<213> ORGANISM: Homo sapiens

<400> SEQUENCE: 23

```
ttgatatctt cattcccatg ttcccaatag ctgctattca caaatgccaa gatttggaag     60

caacctacat gtccatcaac agatgaatgg gtaaagagag tacttcactt atgcacaatg    120

gagtacaatt cagccatgaa aaaagcatga gatcctgtcc tttataataa taacgtggct    180

ggaactcagg tcattatgtt aggtaaaata agccaggcac acaaagacag acattgcatg    240

ttctcactta tttgtgggat ctacaaatca aaacaattga gctaatgtct gggtcttagt    300
```

-continued

```
caattttgta ccctaagtac agggagcaca gccattagaa tacatgatga atgctttaat    360
acaggaatga ataggtgaga ggcacagggt ggttgggtgt tcttctgata catagtatct    420
tccttgacac attcagtaca actctcaaca ggtaagtctc ttcatgtatg ttaccttctg    480
aggaattaag tggcagaaca tgccttctat tattttcctt tgcagaacaa gaccaattgc    540
attagttggg aaacagtgct ggctgcatct gagccccaag caaccattag tctattgcta    600
tcaccacaga ctcagagggg atgacacaca ggggcccagc aatctcaccc aagtcaactc    660
caccaacatt tctggtcacc caccatgtgt acagtacctg ctagggtcca gggtcatgaa    720
agtaaataat accagactgt gcccttgagg aactcacctc tgctaaggga aacaggcaca    780
gaaacccaca agggtggtag agaggaaata ggacaatagg actgtgtgag ggggatagga    840
ggcacccaga ggaggaaatg gttacatctg tgtgaggagg ttggtaagga aagactttaa    900
tagaaggggt ctgtctggct gggcttgcaa ggatgtgtag gagtcatcta gggggcacaa    960
gtacactcca ggcagaggga attgcatggg taaagatctg cagttgtggc ttgtgggatg   1020
gatttcaagt attctggaat gaagacagcc atggaaacaa gggcaggtga gaggatattt   1080
aagaggcttc atgcaatggc tccacttcag tttctgataa gaactcaggt tccgtggact   1140
ccctgataaa actgattaag ttgtttatga ttccccatag aatatgaact caaaggaggt   1200
aagcaaaggg gtgtgtgcga ttctttgcta cctgtcgagc tgcagcccca cctccttctc   1260
cagcacataa acatttcagc agcttgacct aagactgctg tgcagggcag ggatgctcca   1320
ggcagacagc ccagcaaaca acagcacaca gctgaaagta agactcagag gagacagttg   1380
aagaaggcaa gtggcgatg                                                1399
```

<210> SEQ ID NO 24
<211> LENGTH: 1540
<212> TYPE: DNA
<213> ORGANISM: Homo sapiens

<400> SEQUENCE: 24

```
tacactcttg gtgtaaatta ttacaaccac tatagagaac agtttggagg ttcctcaaaa     60
cattaaaaca ttaaaatgga cctatcataa gatccagaaa tcccggtgct gggtataaac    120
caggaagaaa ggaaatccat atattgaaga gatatcttca ttcccatgtt cccaatagct    180
gctattcaca aatgccaaga tttggaagca acctacatgt ccatcaacag atgattgggt    240
aaagagagta cttcacttat gcacaatgga gtacaattca gccatgaaaa aagcatgaga    300
tcctgtcctt tataatagcg tggctggact gcaggtcatt atgttaggta aaataagcca    360
ggcacacaaa gacagacatt gcatgttctc acttatttgt gggatctaca aatcaaaaca    420
attgagctaa tgtctgggtc ttagtcaatt ttgtacccta agtacaggga gcacagccat    480
tagaatacat gatgaatgct ttaatacagg aatgaatagg tgagaggcat cagggtggtt    540
gggtgttctt ctgatacata gttatcttcc ttgacacatt cagtacaact ctcaacagta    600
agtctcttca tgtatgttag cttctgagaa attaaagtga cagaacatga ccttctatta    660
ttttcctttg cagaacaaga ccaattgcat tagttgggaa acagtgctgg ctgcatctga    720
gccccaagca accattagtc tattgctatc accacagact cagaggggat gacacacagg    780
ggcccagcaa tctcacccaa gtcaactcca ccaacatttc tggtcaccca ccatgtgtac    840
agtacctgct aggtccaggg tcatgaaagt aaataatacc agactgtgcc cttagaactc    900
acctctgcta aggaaacagg cacagaaacc acaagggtgg tagagaggaa ataggacaat    960
```

-continued

```
aggactgtgt gagggggata ggaggcaccc agaggaggaa atggttacat ctgtgtgagg   1020

aggttggtaa ggaaagactt taatagaagg gtctgtctgg ctggcgtgca aggatgtgta   1080

ggagtcatct agggggcaca agtacactcc aggcagaggg aattgcatgg taaagatctg   1140

cagttgtggc ttgtggggat ggatttcaag tattctggaa tgaagacagc catggaaaca   1200

agggcaggtg agaggatatt taagaggctt catgccaatg gctccacttc agtttctgat   1260

aagaactcag gttccgtgga ctccctgata aaactgatta agttgtttat gattccccat   1320

agaatatgaa ctcaaaggag gtaagcaaag gggtgtgtgc gattctttgc tacctggcag   1380

ctgcagcccc gcctccttct ccagcacata aacatttcag cagcttgacc taagactgct   1440

gtgcagggca gggatgctcc aggcagacag cccagcaaac aacagcacac agctgaaagt   1500

aagactcaga ggagacagtt gaagaaggca agtggcgatg                         1540
```

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 25
agctgcagcc ccacctcctt ctccagc 27

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 26
agctgcagcc ccgcctcctt ctccagc 27

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 27
tctgtctggc tgggcttgca aggatgtgta g 31

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 28
tctgtctggc tgggcttgca aggatgtgta g 31